United States Patent
Roberts et al.

(10) Patent No.: US 8,759,372 B2
(45) Date of Patent: Jun. 24, 2014

(54) N-(5S,6S,9R)-AMINO-6-(2,3-DIFLUOROPHENYL)-6,7,8,9-TETRAHYDRO-5H-CTCLOHEPTA[B]PYRIDIN-9-YL-4-(2-OXO-2,3-DIHYDRO-1H-IMIDAZO[4,5-B]PYRIDIN-1-CARBOXYLATE SALT

(71) Applicant: Bristol-Myers Squibb Company, Princeton, NJ (US)

(72) Inventors: Daniel Richard Roberts, Robbinsville, NJ (US); Richard Raymond Schartman, Wallingford, CT (US); Chenkou Wei, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/775,528

(22) Filed: Feb. 25, 2013

(65) Prior Publication Data

US 2013/0225636 A1      Aug. 29, 2013

Related U.S. Application Data

(60) Provisional application No. 61/603,598, filed on Feb. 27, 2012.

(51) Int. Cl.
*C07D 401/14*       (2006.01)
*A61K 31/444*       (2006.01)

(52) U.S. Cl.
CPC ............ *A61K 31/444* (2013.01); *C07D 401/14* (2013.01)
USPC .......................................... 514/303; 546/118

(58) Field of Classification Search
CPC ........................... C07D 401/14; A61K 31/444
USPC .......................................... 514/303; 546/118
See application file for complete search history.

(56) References Cited

U.S. PATENT DOCUMENTS

| | | | |
|---|---|---|---|
| 8,044,043 B2 | 10/2011 | Luo | |
| 8,143,403 B2 | 3/2012 | Leahy et al. | |
| 8,314,117 B2 | 11/2012 | Luo et al. | |
| 2012/0245356 A1 | 9/2012 | Leahy et al. | |
| 2013/0096130 A1 | 4/2013 | Luo et al. | |

FOREIGN PATENT DOCUMENTS

| | | |
|---|---|---|
| EP | 1 726 590 | 11/2006 |
| WO | WO 2004/092166 | 10/2004 |
| WO | WO 2004/092168 | 10/2004 |
| WO | WO 2006/044504 | 4/2006 |
| WO | WO 2006/047196 | 5/2006 |
| WO | WO 2007/120590 | 10/2007 |
| WO | WO 2011/046997 | * 4/2011 |

OTHER PUBLICATIONS

Prasad, C.V.C. et al, "Enantioselective synthesis of aminobenzazepinones", Tetrahedron Letters, vol. 48, No. 15, pp. 2661-2665 (2007).

* cited by examiner

*Primary Examiner* — Niloofar Rahmani
(74) *Attorney, Agent, or Firm* — James Epperson

(57) ABSTRACT

Disclosed is a hemisulfate salt of Compound (I):

(I)

and crystalline forms of the hemisulfate salt. Also disclosed are methods of using the hemisulfate salt of Compound (I) as a CGRP receptor antagonist, and pharmaceutical compositions comprising the hemisulfate salt of Compound (I). The hemisulfate salt of Compound (I) is useful in treating, preventing, or ameliorating disorders including migraine and other headaches, neurogenic vasodilation, neurogenic inflammation, thermal injury, circulatory shock, flushing associated with menopause, airway inflammatory diseases such as asthma, and chronic obstructive pulmonary disease (COPD).

8 Claims, 8 Drawing Sheets

N-(5S,6S,9R)-AMINO-6-(2,3-DIFLUOROPHENYL)-6,7,8,9-TETRAHYDRO-5H-CTCLOHEPTA[B]PYRIDIN-9-YL-4-(2-OXO-2,3-DIHYDRO-1H-IMIDAZO[4,5-B]PYRIDIN-1-CARBOXYLATE SALT

CROSS-REFERENCE TO RELATED APPLICATIONS

This application claims the benefit of U.S. Provisional Application Ser. No. 61/603,598 filed Feb. 27, 2012.

BACKGROUND OF THE INVENTION

Disclosed is a hemisulfate salt of N-(5S,6S,9R)-5-amino-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate, as well as crystalline forms thereof. Also disclosed are at least one pharmaceutical composition comprising the hemisulfate salt of N-(5S,6S,9R)-5-amino-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate and at least one method of using the hemisulfate salt of N-(5S,6S,9R)-5-amino-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate in the treatment of a CGRP-related disorder, such as migraine headaches and asthma.

The compound, N-(5S,6S,9R)-5-amino-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate, has the structure of formula I:

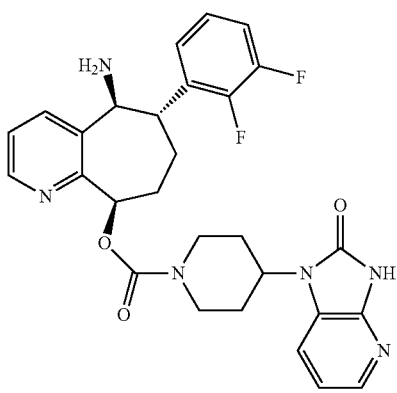

(I)

and is referred to herein as "Compound (I)". Compound (I), processes to prepare Compound (I), and methods of treatment employing Compound (I) are disclosed in U.S. Patent Publication 2011/0251223 A1. This reference is assigned to the present assignee and is incorporated herein by reference in its entirety.

The usefulness of an oral formulation is dependent upon, among other things, the degree to which the active agent is bioavailable and consistency in bioavailability among patients. The bioavailability of orally administered drugs is often affected by various factors including, for example, the solubility of the drug in the gastrointestinal tract, the stability of the drug in the gastrointestinal tract, and drug absorption in the gastrointestinal tract. Further, these factors may be affected by coadministration of other drugs and/or the intake of food, which may lead to variability in the bioavailability of orally administered drug. Furthermore, rapid in vivo dissolution of the active agent is also required to provide rapid treatment of conditions such as migraine headaches.

The dissolution rate of Compound (I) is dependent on the pH of the aqueous medium. Compound (I) has a higher dissolution rate at pH values of 1 and 5 than at a pH value of 7. In the oral administration of Compound (I), the dissolution rate and hence the bioavailability of Compound I can be affected by the pH of the stomach contents. The normal pH of the stomach is 1.2 to 1.8 according to C. J. Perigard, *Clinical Analysis*, Chapter 32, in *Remington: The Science and Practice of Pharmacy* $20^{th}$ Edition, A. R. Gennaro, editor; 2000, Lippinocott Williams & Wilkins, Baltimore, Md. However, patients often take other medications that can raise the pH of the stomach, including antacids, proton pump inhibitors, and $H_2$-receptor antagonists such as famotidine, which can lower the dissolution rate of Compound (I).

Typically, in preparing a pharmaceutical composition, a form of the active ingredient is sought that has a balance of desired properties, such as, for example, dissolution rate, solubility, bioavailability, and/or storage stability. For example, a form of the active ingredient is sought having sufficient stability, solubility, and bioavailability to prevent the sufficiently soluble and bioavailable form from converting during the manufacture, preparation, and/or storage of the pharmaceutical composition to another form having an undesirable solubility and/or bioavailability profile. For example, a form of the active ingredient is sought that is stable and has low hygroscopicity at ambient temperature and humidity conditions.

In addition, a form of the active ingredient may also be sought that permits the active ingredient to be produced by a process that is amendable to large-scale production. In such a process, it is desirable that active ingredient is in a form that allows facile isolation and/or purification of the active ingredient, for example, by filtration, as well as easy drying.

Further, as production economics are important, it is desirable to avoid the use of higher cost materials, whenever possible, in the preparation of the form.

Applicants have found a hemisulfate salt of Compound (I) that surprisingly reduces the variability in the bioavailability of Compound (I), provides consistency in bioavailability among patients, and/or increases the bioavailability of Compound (I) to the patient. Further, Applicants have also found a crystalline form of the hemisulfate salt of Compound (I) that surprisingly reduces the variability in the bioavailability of Compound (I), provides consistency in bioavailability among patients, and/or increases the bioavailability of Compound (I) to the patient. The hemisulfate salt of Compound (I) and the crystalline form thereof, surprisingly afford a balance of properties sought in a pharmaceutical composition. The present invention is also directed to other important aspects.

SUMMARY OF THE INVENTION

One aspect of the invention is a hemisulfate salt of Compound (I):

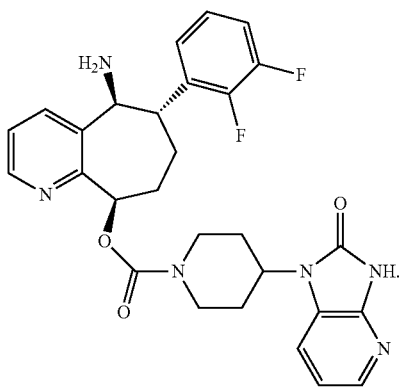

(I)

The present invention also provides a crystalline form of the hemisulfate salt of Compound (I).

The present invention also provides pharmaceutical compositions comprising a pharmaceutically acceptable carrier and/or diluent; and the hemisulfate salt of Compound (I).

The present invention also provides a method of treating a disease or disorder associated with the activity of the CGRP receptor, the method comprising administering to a mammalian patient the hemisulfate salt of Compound (I).

The present invention also provides processes and intermediates for making the hemisulfate salt of Compound (I), and/or crystalline forms thereof.

The present invention also provides the hemisulfate salt of Compound (I) for use in therapy.

The present invention also provides the hemisulfate salt of Compound (I) for the manufacture of a medicament for the treatment of migraine headaches, neurogenic vasodilation, neurogenic inflammation, thermal injury, circulatory shock, flushing associated with menopause, airway inflammatory diseases such as asthma, and chronic obstructive pulmonary disease (COPD).

These and other features of the invention will be set forth in expanded form as the disclosure continues.

DETAILED DESCRIPTION

Figure 1:
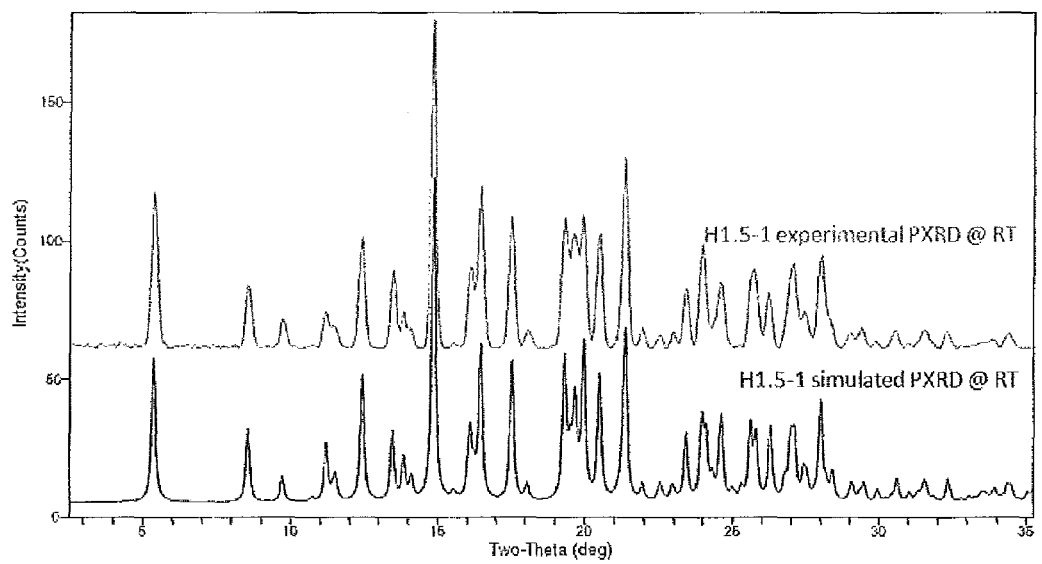
FIG. 1 shows the experimental (at room temperature) and simulated (room temperature) PXRD patterns (CuKα λ=1.5418 Å) of Form H1.5-1 of Example 1.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

The names used herein to characterize a specific form, e.g., "H1.5-1", "P22C", "P33", and "P35", are merely identifiers that are to be interpreted in accordance with the characterization information presented herein and are not to be limited so as to exclude any other substance possessing similar or identical physical and chemical characteristics.

The definitions set forth herein take precedence over definitions set forth in any patent, patent application, and/or patent application publication incorporated herein by reference.

All numbers expressing quantities of ingredients, weight percentages, temperatures, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

All measurements are subject to experimental error and are within the spirit of the invention.

The hemisulfate salt of Compound (I) is, subsequent to its preparation, preferably isolated and purified to obtain a composition containing an amount by weight equal to or greater than 99%, preferably 99.5%, and more preferably, 99.9%, of the hemisulfate salt of Compound (I)) ("substantially pure"), which is then used or formulated as described herein. Such "substantially pure" hemisulfate salt of Compound (I) is also contemplated herein as part of the present invention.

As used herein, "polymorphs" refer to crystalline forms having the same chemical structure but different spatial arrangements of the molecules and/or ions forming the crystals.

As used herein, "amorphous" refers to a solid form of a molecule and/or ion that is not crystalline. An amorphous solid does not display a definitive X-ray diffraction pattern with sharp maxima.

As used herein, the term "substantially pure crystalline form" means the crystalline form of Compound (I) hemisulfate salt referred to contains at least about 90 wt. % of that form, based on the weight of the Compound (I) hemisulfate salt. The term "at least about 90 wt. %," while not intending to limit the applicability of the doctrine of equivalents to the scope of the claims, includes, but is not limited to, for example, about 90, 90, about 91, 91, about 92, 92, about 93, 93, about 94, 94, about 95, 95, about 96, 96, about 97, 97, about 98, 98, about 99, 99, and about 100 wt. %, based on the weight of the Compound (I) hemisulfate salt. The remainder of the Compound (I) hemisulfate salt may comprise other Form(s) of the Compound (I) hemisulfate salt including amorphous Compound (I) hemisulfate salt and/or reaction impurities and/or processing impurities that arise, for example, when the hemisulfate salt is prepared and/or when the crystalline form is prepared.

The presence of reaction impurities and/or processing impurities may be determined by analytical techniques known in the art, such as, for example, chromatography, nuclear magnetic resonance spectroscopy, mass spectrometry, and/or infrared spectroscopy.

As used herein, the parameter "molecules/asymmetric unit" refers to the number of molecules of Compound (I) in the asymmetric unit.

As used herein, the unit cell parameter "molecules/unit cell" refers to the number of molecules of Compound (I) in the unit cell.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The first aspect of the invention provides the hemisulfate salt of Compound (I),

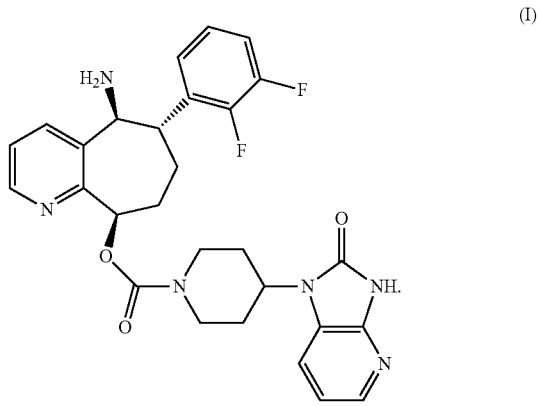 [SMILES: N[C@@H]1c2cccnc2[C@H](OC(=O)N2CCC(n3c(=O)[nH]c4ncccc43)CC2)CC[C@H]1c1cccc(F)c1F]

(I)

The hemisulfate salt of Compound (I) is an acid salt of Compound (I) having a ratio of 0.5 $H_2SO_4$ molecule to each molecule of Compound (I), and has the name: (5S,6S,9R)-5-amino-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate, hemisulfate salt.

In one embodiment, the hemisulfate salt of Compound (I) is provided as a sesquihydrate, having a ratio of 1.5 water molecules and 0.5 $H_2SO_4$ molecule for each molecule of Compound (I).

In one embodiment, the hemisulfate salt of Compound (I) is provided as a crystalline form.

In one embodiment, the hemisulfate salt of Compound (I) is provided as a crystalline form, wherein the crystalline form is Form H1.5-1. This crystalline form has a ratio of 1.5 water molecules and 0.5 $H_2SO_4$ molecule for each molecule of Compound (I).

In one embodiment, Form H1.5-1 is characterized by unit cell parameters substantially equal to the following:
Cell dimensions:
a=10.92 Å
b=33.04 Å
c=7.90 Å
α=90 degrees
β=90 degrees
γ=90 degrees
Space group: $P2_12_12$
Molecules of Compound (I)/asymmetric unit: 1
Volume=2851 Å$^3$
Density (calculated)=1.423 g/cm$^3$,
wherein measurement of said crystalline form is at a temperature of about 25° C.

In one embodiment, Form H1.5-1 is characterized by an observed powder x-ray diffraction pattern substantially in accordance with the pattern shown in FIG. 1.

In one embodiment, Form H1.5-1 is characterized by a simulated powder x-ray diffraction pattern substantially in accordance with the pattern shown in FIG. 1.

In one embodiment, Form H1.5-1 is characterized by a powder x-ray diffraction pattern (CuKα λ=1.5418 Å) comprising four or more, preferably five or more, 2θ values selected from: 5.4±0.1, 8.6±0.1, 9.7±0.1, 12.4±0.1, 14.9±0.1, 17.6±0.1, 18.1±0.1, 20.5±0.1, 21.4±0.1, and 22.0±0.1, wherein measurement of the crystalline form is at a temperature of about 25° C.

Figure 4:
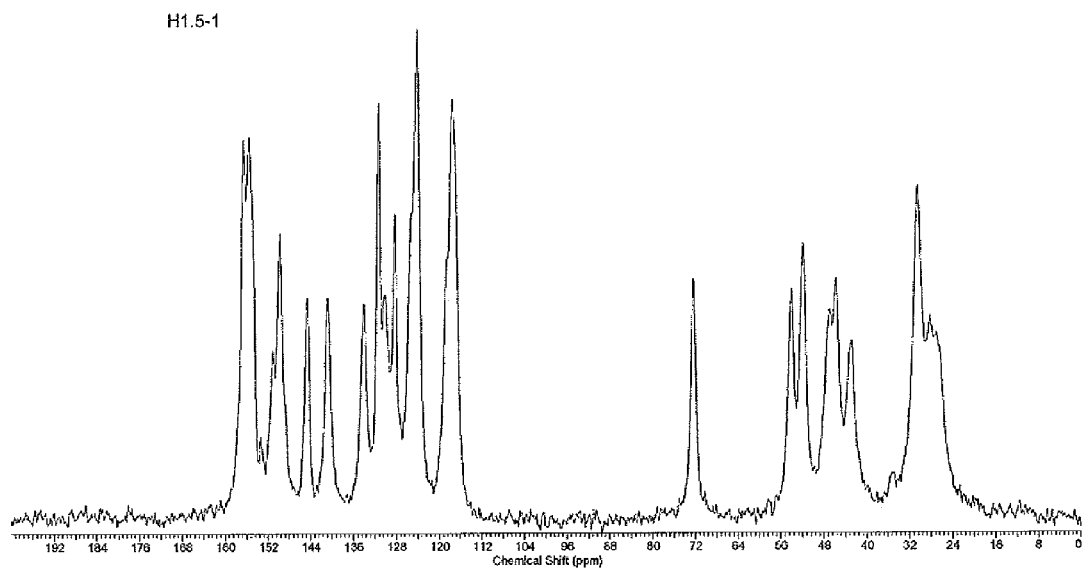
FIG. 4 shows the charge polarized magic angle spinning (CPMAS) NMR spectrum of Form H1.5-1 of Example 1.

In another embodiment, the Form H1.5-1 is characterized by a solid state nuclear magnetic resonance spectra (ssNMR) substantially in accordance with the spectra shown in FIG. 4.

In one embodiment, Form H1.5-1 is characterized by a solid state nuclear resonance spectra comprising six or more, preferably seven or more peaks (δ (ppm) referenced to TMS) selected from: 26.6±0.1, 27.1±0.1, 28.3±0.1, 30.7±0.1, 43.1±0.1, 45.9±0.1, 47.1±0.1, 52.0±0.1, 54.2±0.1, 72.5±0.1, 117.0±0.1, 117.7±0.1, 124.2±0.1, 125.2±0.1, 128.3±0.1, 130.3±0.1, 131.4±0.1, 134.1±0.1, 140.8±0.1, 144.7±0.1, 148.7±0.1, 149.8±0.1, 151.2±0.1, 153.4±0.1, 155.1±0.1, 155.6±0.1, and 156.7±0.1.

In yet an even further embodiment, the Form H1.5-1 is characterized by fractional atomic coordinates substantially as listed in Table 1.

TABLE 1

Fractional Atomic Coordinates of Form H1.5-1 Calculated at 25° C. Atomic coordinates (×10$^4$) of Non-hydrogen Atoms and Equivalent Isotropic Displacement Parameters (Å$^2$ × 10$^3$)

| | x | y | z | U(eq) |
|---|---|---|---|---|
| C(1) | 7702(3) | 8678(1) | 5047(4) | 45(1) |
| C(2) | 7665(3) | 8376(1) | 6299(4) | 43(1) |
| C(3) | 9272(3) | 8790(1) | 6797(4) | 44(1) |
| C(4) | 6025(4) | 8432(1) | 3770(5) | 70(1) |
| C(5) | 5920(4) | 8128(1) | 4927(5) | 68(1) |
| C(6) | 6764(3) | 8087(1) | 6238(5) | 58(1) |
| C(7) | 9084(3) | 8223(1) | 8839(4) | 46(1) |
| C(8) | 9695(3) | 7827(1) | 8327(5) | 54(1) |
| C(9) | 10218(3) | 7622(1) | 9881(5) | 63(1) |
| C(10) | 8686(4) | 7945(1) | 11700(4) | 58(1) |
| C(11) | 8134(3) | 8159(1) | 10190(4) | 53(1) |
| C(12) | 8697(3) | 7218(1) | 11470(4) | 45(1) |
| C(13) | 7480(3) | 6816(1) | 6484(5) | 63(1) |
| C(14) | 6737(4) | 6498(1) | 6034(5) | 66(1) |
| C(15) | 6572(3) | 6186(1) | 7183(5) | 56(1) |
| C(16) | 7163(3) | 6198(1) | 8726(4) | 45(1) |
| C(17) | 7940(3) | 6527(1) | 9039(4) | 46(1) |
| C(18) | 7080(3) | 5870(1) | 10058(4) | 47(1) |
| C(19) | 8201(3) | 5591(1) | 10055(4) | 48(1) |
| C(20) | 9403(3) | 5815(1) | 9660(5) | 54(1) |
| C(21) | 9708(3) | 6200(1) | 10646(5) | 54(1) |
| C(22) | 8709(3) | 6526(1) | 10646(4) | 47(1) |
| C(23) | 8230(3) | 5323(1) | 11619(4) | 49(1) |
| C(24) | 8222(3) | 4904(1) | 11444(5) | 64(1) |
| C(25) | 8278(3) | 4654(2) | 12797(7) | 85(1) |
| C(26) | 8326(4) | 4790(2) | 14381(7) | 88(1) |
| C(27) | 8409(4) | 5198(2) | 14617(6) | 87(1) |
| C(28) | 8331(4) | 5461(1) | 13244(5) | 72(1) |
| N(1) | 8644(2) | 8451(1) | 7370(3) | 45(1) |
| N(2) | 8677(2) | 8920(1) | 5375(3) | 48(1) |
| N(3) | 6912(3) | 8717(1) | 3793(4) | 60(1) |
| N(4) | 9279(3) | 7571(1) | 11190(4) | 53(1) |
| N(5) | 8091(3) | 6835(1) | 7965(4) | 54(1) |
| N(6) | 5959(2) | 5617(1) | 9862(4) | 53(1) |
| O(1) | 10190(2) | 8933(1) | 7438(3) | 62(1) |
| O(2) | 7746(2) | 7179(1) | 12241(3) | 62(1) |
| O(3) | 9356(2) | 6904(1) | 10833(3) | 51(1) |
| O(4) | 3908(2) | 4985(1) | 7592(3) | 66(1) |
| O(5) | 4930(3) | 5364(1) | 5467(3) | 75(1) |
| S(1) | 500010 | 5000 | 6494(1) | 46(1) |
| O(1S) | 500010 | 500010 | 2134(5) | 82(1) |
| O(2S) | 3401(3) | 5784(1) | 8737(4) | 80(1) |
| F(1) | 8437(3) | 5844(1) | 13581(3) | 87(1) |
| F(2) | 8604(3) | 5343(1) | 16124(3) | 108(1) |
| F(1A) | 8206(8) | 4781(5) | 9853(10) | 114(6) |
| F(2A) | 8316(9) | 4256(2) | 12660(30) | 159(8) |

*The difluorophenyl ring is found disordered in the crystal over two orientations (F1/F1A, F2/F2A) with occupancies of 0.817(5) and 0.183(5).

TABLE 2

Table 2: Fractional Atomic Coordinates of Form H1.5-1 Calculated at 25° C. Atomic coordinates (×10$^4$) of Hydrogen Atoms and Equivalent Isotropic Displacement Parameters (Å$^2$ × 10$^3$)

| | x | y | z | U(eq) |
|---|---|---|---|---|
| H(4) | 5448 | 8444 | 2906 | 84 |
| H(5) | 5274 | 7946 | 4840 | 82 |
| H(6) | 6720 | 7877 | 7021 | 69 |
| H(7) | 9727 | 8389 | 9355 | 55 |
| H(8A) | 9099 | 7650 | 7791 | 64 |
| H(8B) | 10345 | 7880 | 7520 | 64 |
| H(9A) | 10543 | 7359 | 9569 | 76 |
| H(9B) | 10887 | 7783 | 10327 | 76 |
| H(10A) | 9281 | 8121 | 12238 | 70 |
| H(10B) | 8047 | 7886 | 12517 | 70 |
| H(11A) | 7467 | 7998 | 9738 | 63 |
| H(11B) | 7803 | 8418 | 10541 | 63 |
| H(13) | 7567 | 7029 | 5727 | 76 |
| H(14) | 6353 | 6493 | 4984 | 80 |
| H(15) | 6064 | 5969 | 6916 | 67 |
| H(18) | 7040 | 6002 | 11167 | 56 |
| H(19) | 8075 | 5406 | 9102 | 58 |
| H(20A) | 10071 | 5626 | 9831 | 65 |
| H(20B) | 9395 | 5884 | 8467 | 65 |
| H(21A) | 10450 | 6316 | 10175 | 65 |
| H(21B) | 9882 | 6126 | 11809 | 65 |
| H(22) | 8173 | 6486 | 11626 | 56 |
| H(24) | 8191 | 4792 | 10344 | 77 |
| H(25) | 8243 | 4381 | 12622 | 101 |
| H(26) | 8303 | 4613 | 15296 | 106 |
| H(2) | 8891 | 9125 | 4774 | 57 |
| H(6A) | 6054 | 5449 | 8992 | 80 |
| H(6B) | 5316 | 5777 | 9675 | 80 |
| H(6C) | 5836 | 5475 | 10803 | 80 |
| H(1SA) | 4864 | 5219 | 2659 | 123 |
| H(2SA) | 3380 | 5533 | 8525 | 120 |
| H(2SB) | 2905 | 5909 | 8107 | 120 |

Figure 2:
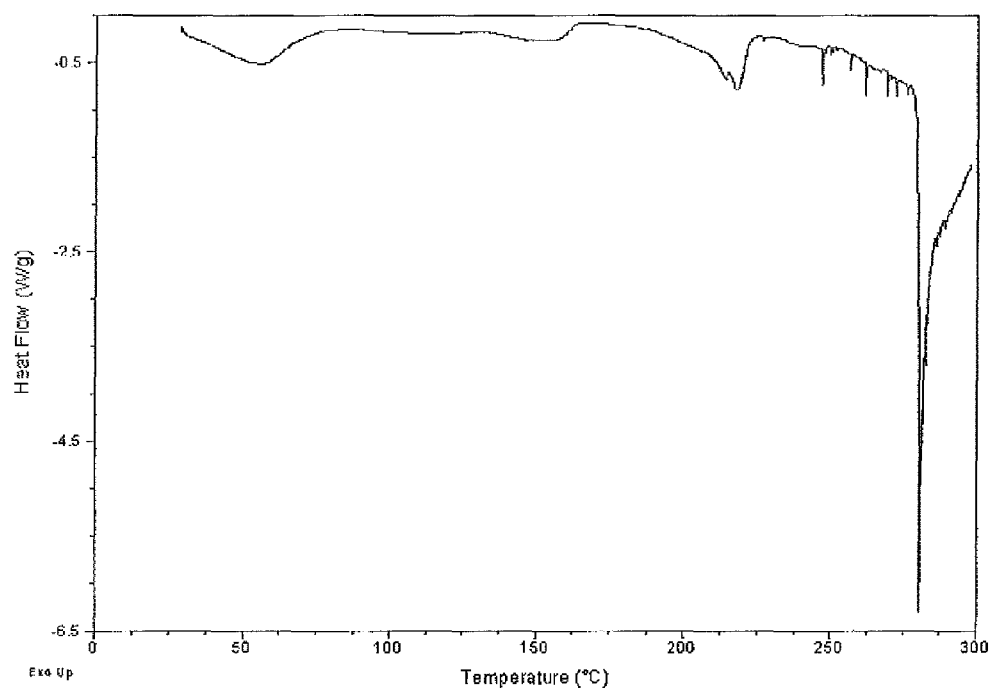
FIG. 2 shows the differential scanning calorimetry profile of Form H1.5-1 of Example 1.

In a still further embodiment, Form H1.5-1 is characterized by a DSC thermogram substantially in accordance with that shown in FIG. 2.

In still another embodiment, the Form H1.5-1 is characterized by a TGA thermogram, wherein the Form H1.5-1 experiences a weight loss of approximately 4-5 weight % upon being heated to a temperature of about 200° C.

Figure 3:
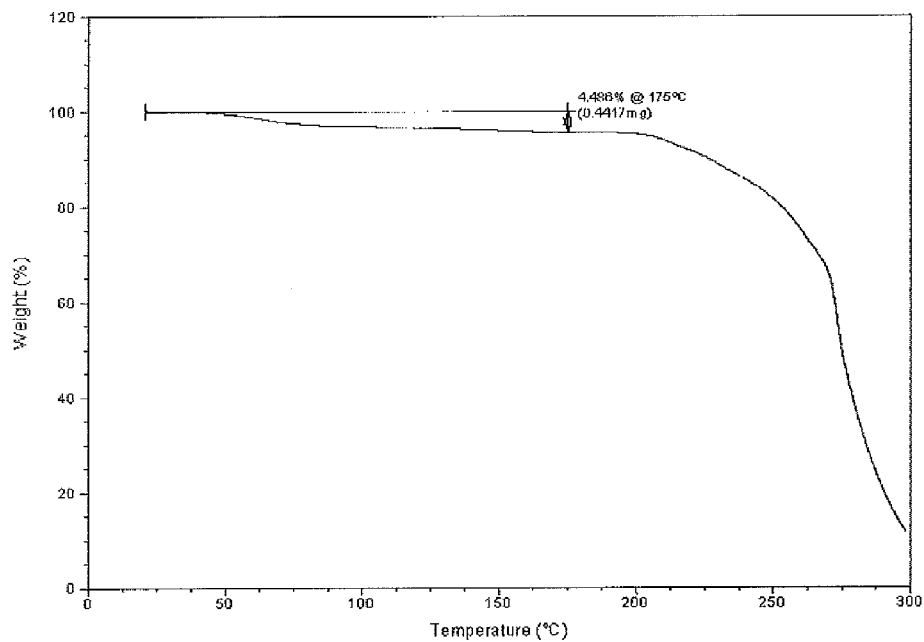
FIG. 3 shows the thermogravimetric analysis profile of Form H1.5-1 of Example 1.

In still an even further embodiment, the Form H1.5-1 exhibits a TGA thermogram substantially the same as shown in FIG. 3.

In still yet another embodiment, Form H1.5-1 is provided in a substantially pure crystalline form.

In still yet an even further embodiment, the hemisulfate salt of Compound (I) contains at least about 90 wt. %, preferably at least about 95 wt. %, and more preferably at least about 99 wt. %, of Form H1.5-1, based on the weight of the hemisulfate salt.

In a still further embodiment, a substantially pure Form H1.5-1 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially pure Form H1.5-1 has substantially pure phase homogeneity with less than about 1% of the total peak area of the experimentally measured PXRD pattern arising from peaks that are absent from the simulated PXRD pattern.

In another embodiment, the hemisulfate salt of Compound (I) consists essentially of Form H1.5-1. The crystalline form of this embodiment may comprise at least about 90 wt. %, preferably at least about 95 wt. %, and more preferably at least about 99 wt. %, based on the weight of the hemisulfate salt of Compound (I).

In yet another embodiment, a pharmaceutical composition comprises the hemisulfate salt of Compound (I) in Form H1.5-1; and at least one pharmaceutically-acceptable carrier and/or diluent.

In one embodiment, the hemisulfate salt of Compound (I) is provided as a crystalline form, wherein the crystalline form is P22C. This crystalline form is a sesquihydrate having a ratio of 1.5 water molecules and 0.5 $H_2SO_4$ molecule for each molecule of Compound (I).

Figure 10:
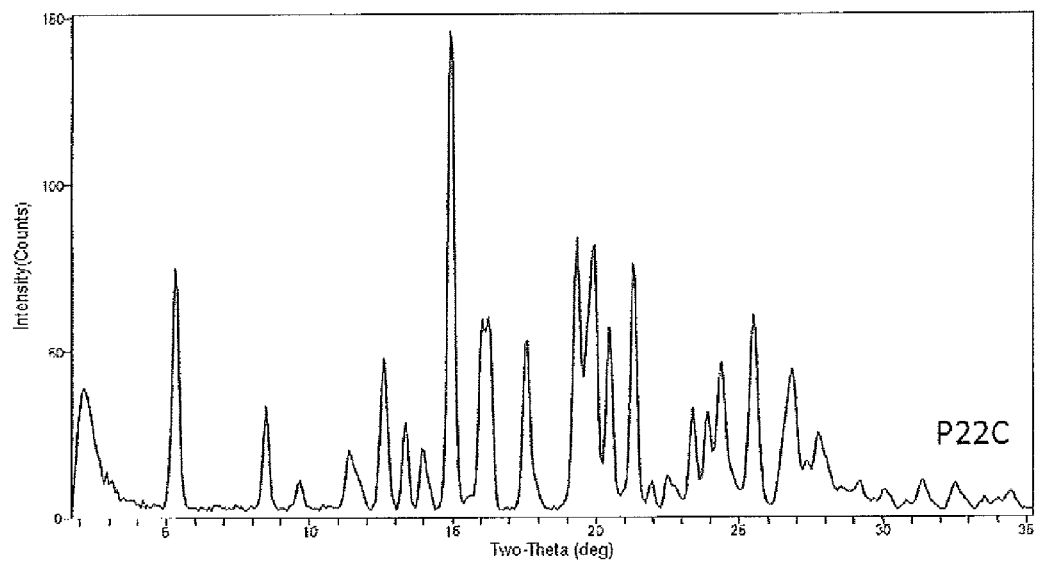
FIG. 10 shows the experimental (at room temperature) PXRD pattern (CuKα λ=1.5418 Å) of Form P22C of Example 1.

In one embodiment, Form P22C is characterized by an observed powder x-ray diffraction pattern substantially in accordance with the pattern shown in FIG. 10.

In one embodiment, the hemisulfate salt of Compound (I) is provided as a monohydrate, having a ratio of one water molecule and 0.5 $H_2SO_4$ molecule for each molecule of Compound (I).

In one embodiment, the hemisulfate salt of Compound (I) is provided as a crystalline form, wherein the crystalline form is Form P33. This crystalline form has a ratio of one water molecule and 0.5 $H_2SO_4$ molecule for each molecule of Compound (I).

Figure 11:
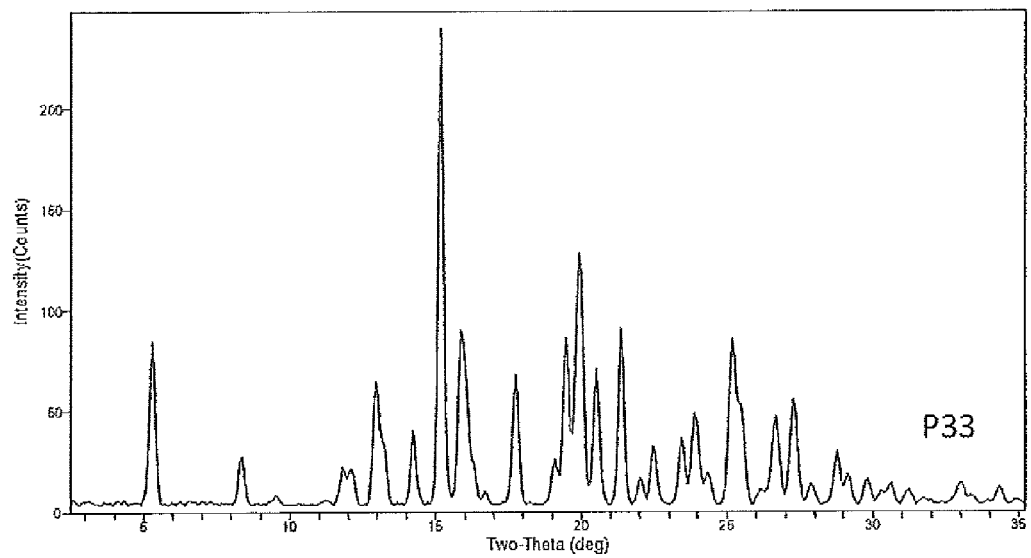
FIG. 11 shows the experimental (at room temperature) PXRD pattern (CuKα λ=1.5418 Å) of Form P33 of Example 1.
Figure 12:
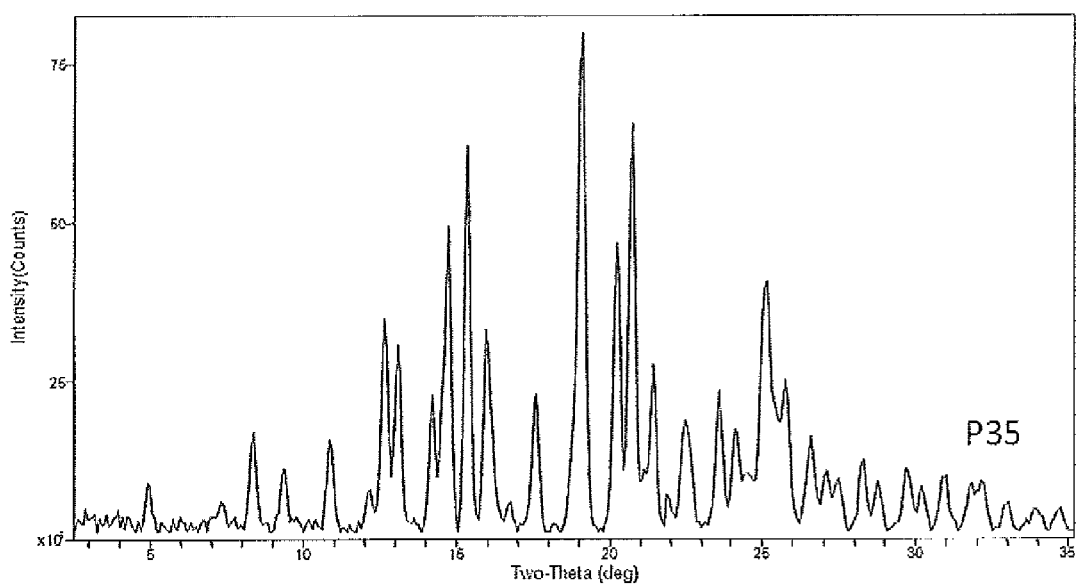
FIG. 12 shows the experimental (at room temperature) PXRD pattern (CuKα λ=1.5418 Å) of Form P35 of Example 1.

In one embodiment, Form P33 is characterized by an observed powder x-ray diffraction pattern substantially in accordance with the pattern shown in FIG. 11.

Compound (I) is suitable as a CGRP receptor antagonist and is useful in the treatment of CGRP related disorders including migraine headaches, neurogenic vasodilation, neurogenic inflammation, thermal injury, circulatory shock, flushing associated with menopause, airway inflammatory diseases such as asthma, and chronic obstructive pulmonary disease (COPD).

Calcitonin gene-related peptide (CGRP) is a naturally occurring 37-amino-acid peptide first identified in 1982 (Amara, S. G. et al, Science 1982, 298, 240-244). Two forms of the peptide are expressed (αCGRP and βCGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, Br J Pharmacol 1992, 105, 441-7; Van Valen, F. et al, Neurosci Lett 1990, 119, 195-8). Two classes of CGRP receptors, CGRP1 and CGRP2, have been proposed based on the antagonist properties of the peptide fragment CGRP(8-37) and the ability of linear analogues of CGRP to activate CGRP2 receptors (Juaneda, C. et al. TiPS 2000, 21, 432-438). However, there is lack of molecular evidence for the CGRP2 receptor (Brain, S. D. et al, TiPS 2002, 23, 51-53). The CGRP1 receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., J Biol Chem. 2000, 275, 31438-43). RAMP1 is required for transport of CRLR to the plasma membrane and for ligand binding to the CGRP-receptor (McLatchie, L. M. et al, Nature 1998, 393, 333-339). RCP is required for signal transduction (Evans B. N. et al., J Biol Chem. 2000, 275, 31438-43). There are known species-specific differences in binding of small molecule antagonists to the CGRP-receptor with typically greater affinity seen for antagonism of the human receptor than for other species (Brain, S. D. et al, TiPS 2002, 23, 51-53). The amino acid sequence of RAMP1 determines the species selectivity, in particular, the amino acid residue Trp74 is responsible for the phenotype of the human receptor (Mallee et al. J Biol Chem 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001; 15(10): 745-53; Williamson, D. J. Microsc. Res. Tech. 2001, 53, 167-178; Grant, A. D. Brit. J. Pharmacol. 2002, 135, 356-362). Serum levels of CGRP are elevated during migraine (Goadsby P J, et al. Ann Neurol 1990; 28:183-7) and treatment with anti-migraine drugs returns CGRP levels to normal coincident with alleviation of headache (Gallai V. et al. Cephalalgia 1995; 15: 384-90). Migraineurs exhibit elevated basal CGRP levels compared to controls (Ashina M, et al., Pain 2000, 86(1-2):133-8. 2000). Intravenous CGRP infusion produces lasting headache in migraineurs (Lassen L H, et al. Cephalalgia 2002 February; 22(1):54-61). Preclinical studies in dog and rat report that systemic CGRP blockade with the peptide antagonist CGRP(8-37) does not alter resting systemic hemodynamics nor regional blood flow (Shen, Y-T. et al, J Pharmacol Exp Ther 2001, 298, 551-8). Thus, CGRP-receptor antagonists may present a novel treatment for migraine that avoids the cardiovascular liabilities of active vasoconstriction associated with non-selective 5-HT1B/1D agonists, 'triptans' (e.g., sumatriptan).

CGRP antagonists have shown efficacy in human clinical trials. See Davis C D, Xu C. Curr Top Med Chem. 2008 8(16):1468-79; Benemei S, Nicoletti P, Capone J G, Geppetti P. Curr Opin Pharmacol. 2009 9(1):9-14. Epub 2009 Jan. 20; Ho T W, Ferrari M D, Dodick D W, Galet V, Kost J, Fan X, Leibensperger H, Froman S, Assaid C, Lines C, Koppen H, Winner P K. Lancet. 2008 372:2115. Epub 2008 Nov. 25; Ho T W, Mannix L K, Fan X, Assaid C, Furtek C, Jones C J, Lines C R, Rapoport A M; Neurology 2008 70:1304. Epub 2007 Oct. 3.

Pharmaceutical Compositions and Methods of Treatment

The hemisulfate salt of Compound (I) inhibits the CGRP receptor. As such, the hemisulfate salt of Compound (I) is useful for treating conditions or disorders associated with aberrant CGRP levels or where modulating CGRP levels may have therapeutic benefit.

Accordingly, another aspect of the invention is a pharmaceutical composition comprising the hemisulfate salt of Compound (I) with a pharmaceutically acceptable adjuvant, carrier, or diluent.

One embodiment provides a pharmaceutical composition comprising a hemisulfate salt of Compound (I) sesquihydrate with a pharmaceutically acceptable adjuvant, carrier, or diluent.

One embodiment provides a pharmaceutical composition comprising a crystalline form of the hemisulfate salt of Compound (I) with a pharmaceutically acceptable adjuvant, carrier, or diluent.

One embodiment provides a pharmaceutical composition comprising a crystalline form of the hemisulfate salt of Compound (I) sesquihydrate with a pharmaceutically acceptable adjuvant, carrier, or diluent.

One embodiment provides a pharmaceutical composition comprising Form H1.5-1 of the hemisulfate salt of Compound (I) with a pharmaceutically acceptable adjuvant, carrier, or diluent.

Compounds are generally given as pharmaceutical compositions comprised of a therapeutically effective amount of the hemisulfate salt of Compound (I), and a pharmaceutically acceptable carrier, and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, lozenges, and powders as well as liquid suspensions, syrups, elixirs, and solutions. Solid compositions may by formed in timed or sustained released formulations. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 0.1 mg, 1 mg, 10 mg, 100 mg, 500 mg, and 1000 mg. Liquid compositions are generally in a unit dosage range of 1-100 mg/mL. Some examples of liquid dosage units are 0.1 mg/mL, 1 mg/mL, 10 mg/mL, 25 mg/mL, 50 mg/mL, and 100 mg/mL.

In one embodiment, an oral dosage form provides 70 to 750 mg of Compound (I) as the hemisulfate salt of Compound (I). Included in this embodiment are oral dosage forms having 70 mg, 80 mg, 90 mg, 100 mg, 150 mg, 200 mg, 250 mg, 300 mg, 500 mg, and 750 mg of the Compound (I) as the hemisulfate salt of Compound (I).

In one embodiment, an oral dosage form provides 70 to 750 mg of Compound (I) as Form H1.5-1 of the hemisulfate salt of Compound (I). Included in this embodiment are oral dosage forms having 70 mg, 80 mg, 90 mg, 100 mg, 150 mg, 200 mg, 250 mg, 300 mg, 500 mg, and 750 mg of the Compound (I) as Form H1.5-1 of the hemisulfate salt of Compound (I).

In one embodiment, the hemisulfate salt of Compound (I) is administered once a day. Suitable doses include 70 mg, 80 mg, 90 mg, 100 mg, 150 mg, 200 mg, 250 mg, 300 mg, 500 mg, and 750 mg of the Compound (I) as Form H1.5-1 of the hemisulfate salt of Compound (I).

In one embodiment, the hemisulfate salt of Compound (I) is administered twice a day. Suitable doses include 70 mg, 80 mg, 90 mg, 100 mg, 150 mg, 200 mg, 250 mg, 300 mg, 500 mg, and 750 mg of the Compound (I) as Form H1.5-1 of the hemisulfate salt of Compound (I).

The invention encompasses all conventional modes of administration including oral, parenteral, intranasal, sublingual, and transdermal methods. Typically, the daily dose will be 0.01-100 mg/kg body weight daily. Generally, more compound is required orally and less parenterally. The specific dosing regimen, however, should be determined by a physician using sound medical judgment.

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001, 15(10), 745-53; Williamson, D. J. Microsc. Res. Tech. 2001, 53, 167-178; Grant, A. D. Brit. J. Pharmacol. 2002, 135, 356-362). Serum levels of CGRP are elevated during migraine (Goadsby P. J. et al. Ann. Neurol. 1990, 28, 183-7) and treatment with anti-migraine drugs returns CGRP levels to normal coincident with alleviation of headache (Gallai V. et al. Cephalalgia 1995, 15, 384-90). Migraineurs exhibit elevated basal CGRP levels compared to controls (Ashina M. et al., Pain 2000, 86(1-2), 133-8). Intravenous CGRP infusion produces lasting headache in migraineurs (Lassen L. H. et al. Cephalalgia. 2002, 22(1), 54-61). Preclinical studies in dog and rat report that systemic CGRP blockade with the peptide antagonist CGRP(8-37) does not alter resting systemic hemodynamics nor regional blood flow (Shen, Y-T. et al. J. Pharmacol. Exp. Ther. 2001, 298, 551-8). Thus, CGRP-receptor antagonists may present a novel treatment for migraine that avoids the cardiovascular liabilities of active vasoconstriction associated with non-selective 5-HT1B/1D agonists, "triptans" (e.g., sumatriptan).

Another aspect of the invention is a method of inhibiting the CGRP receptor comprising contacting the CGRP receptor with the hemisulfate salt of Compound (I).

One embodiment provides a method of inhibiting the CGRP receptor comprising contacting the CGRP receptor with the hemisulfate salt of Compound (I) sesquihydrate.

One embodiment provides a method of inhibiting the CGRP receptor comprising contacting the CGRP receptor with a crystalline hemisulfate salt of Compound (I) sesquihydrate.

One embodiment provides a method of inhibiting the CGRP receptor comprising contacting the CGRP receptor with Form H1.5-1 of the hemisulfate salt of Compound (I).

Another aspect of the invention is a method for treating conditions associated with aberrant levels of CGRP comprising the administration of a therapeutically effective amount of the hemisulfate salt of Compound (I) to a patient.

Another aspect of the invention is the use of the hemisulfate salt of Compound (I) in the manufacture of a medicament for the treatment of conditions related to aberrant levels of CGRP.

Another aspect of the invention is a method of treating migraine or headache.

Another aspect of the invention relates to a method of treating inflammation (particularly neurogenic inflammation), pain, thermal injury, circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising the hemisulfate salt of Compound (I) as defined herein.

Another aspect of the invention relates to methods selected from the group consisting of (a) immune regulation in gut mucosa (b) protective effect against cardiac anaphylactic injury (c) stimulating or preventing interleukin-1b(IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, Stefanie; Knauer, Jens; Haberberger, Rainer; Goeke, Burkhard; Voigt, Karlheinz; McGregor, Gerard Patrick. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, Wei-Qing; Du, Yan-Hua; Hu, Chang-Ping; Ye, Feng; Tan, Gui-Shan; Deng, Han-Wu; Li, Yuan-Jian. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1. Lian, Kai; Du, Jingyuan; Rao, Zhenyu; Luo, Huaican. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokinin) receptors by rat spinal neurons. Seybold V S, McCarson K E, Mermelstein P G, Groth R D, Abrahams L G. J. Neurosci. 2003 23 (5): 1816-1824. Department of Neuroscience, University of Minnesota, Minneapolis, Minn. 55455, and Department of Pharmacology, Toxicology, and Therapeutics, University of Kansas Medical Center, Kansas City, Kans. 66160 (e) Attenuation of antigen-induced airway hyperresponsiveness in CGRP-deficient mice. Aoki-Nagase, Tomoko; Nagase, Takahide; Oh-Hashi, Yoshio; Shindo, Takayuki; Kurihara, Yukiko; Yamaguchi, Yasuhiro; Yamamoto, Hiroshi; Tomita, Tetsuji; Ohga, Eijiro; Nagai, Ryozo; Kurihara, Hiroki; Ouchi, Yasuyoshi. Department of Geriatric Medicine, Graduate School of Medicine, University of Tokyo, Tokyo, Japan. American Journal of Physiology (2002), 283(5, Pt. 1), L963-L970; (f) Calcitonin gene-related peptide as inflammatory mediator. Springer, Jochen; Geppetti, Pierangelo; Fischer, Axel; Groneberg, David A. Charite Campus-Virchow, Department of Pediatric Pneumology and Immunology, Division of Allergy Research, Humboldt-University Berlin, Berlin, Germany Pulmonary Pharmacology & Therapeutics (2003), 16(3), 121-130; and (g) Pharmacological targets for the inhibition of neurogenic inflammation. Helyes, Zsuzsanna; Pinter, Erika; Nemeth, Jozsef; Szolcsanyi, Janos. Department of Pharmacology and Pharmacotherapy, Faculty of Medicine, University of Pecs, Pecs, Hung. Current Medicinal Chemistry: Anti-Inflammatory & Anti-Allergy Agents (2003), 2(2), 191-218.

Another aspect of this invention relates to a method of treatment using combinations of the hemisulfate salt of Compound (I) with one or more agents selected from the group consisting of COX-2 inhibitors, NSAIDS, aspirin, acetaminophen, triptans, ergotamine and caffeine for the treatment of migraine.

"Migraine," "headache," and related terms are as understood by medical practitioners. Migraine encompasses all classes of migraine including common, classic, cluster, fulgurating, hemiplegic, opthalmoplegic, and opthomalmic.

By "therapeutically effective amount" is meant an amount that when administered either alone, or in combination with an additional therapeutic agent is effective to prevent, suppress, and/or ameliorate a disease and/or condition and/or the progression of a disease and/or condition.

"Patient" means a person who may benefit from treatment as determined by medical practitioners.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

ABBREVIATIONS

DMSO dimethylsulfoxide
EDTA ethylenediaminetetraacetic acid
eq equivalents)
ESI electrospray ionization mass spectroscopy
g gram(s)
h hour(s)
L liter(s)
LCMS liquid chromatography mass spectrometry
M molar
mg milligram(s)
min minute(s)
mL milliliter(s)
mmol millimole(s)
MS mass spectrometry
N normal
NaHMDS sodium bis(trimethylsilyl)amide
NCS N-chlorosuccinimide
NMR nuclear magnetic resonance spectroscopy
RT retention time
ssNMR solid state nuclear magnetic resonance
TBAF tetrabutylammonium fluoride
TFA trifluoroacetic acid
THF tetrahydrofuran
TIPSO triisopropylsilyloxy
TMS tetramethylsilane
μL microliter(s)
° C. degrees Celsius Proton magnetic resonance ($^1$H NMR) spectra were recorded on a Bruker AC 300 or AC 500. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak. Low resolution mass spectra (MS) and the apparent molecular (MH$^+$) or (M–H)$^+$ was determined on a Micromass platform. Elemental analyses are reported as percent by weight. The products were purified by Preparative HPLC using the column YMC S5 ODS (30×100 mm) at a flow rate of 40.0 mL/min and gradient time of 8.0 min. starting from solvent composition of 40% methanol-60% water-0.1% TFA and ending with solvent composition 95% methanol-5% water-0.1% TFA. The products were analyzed by a HPLC instrument using an XTERA column (3.0×50 mm S7) starting from solvent A (10% methanol-90% water-0.1% trifluoroacetic acid (TFA)) and reaching solvent B (10% water-90% methanol-0.1% TFA) over a gradient time of 2 min. The flow rate is 5 mL/min. and retention time (Rf) of product was measured at 220 nm wavelength.

Intermediate 1

(6S,9R)-6-(2,3-Difluorophenyl)-9-hydroxy-6,7,8,9-tetrahydro-5H-cyclohepta[b]pyridin-5-one

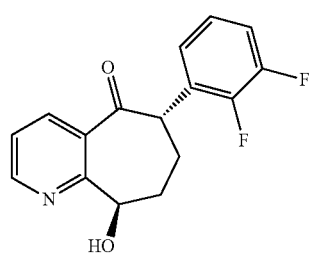

(Int.1)

In a 250 mL round-bottom flask was dissolved (9R)-6-(2,3-difluorophenyl)-9-(triisopropylsilyloxy)-6,7,8,9-tetrahydro-5H-cyclohepta[b]pyridin-5-one (0.218 g, 0.49 mmol) in tetrahydrofuran (5 mL) to give a colorless solution. After cooling to −15° C. (ice-methanol bath) under nitrogen, TBAF (0.490 mL, 0.490 mmol) was added, and the resulting bright yellow solution was stirred at −15° C. for 1 h. It was quenched with sodium bicarbonate solution and diluted with ethyl acetate. The layers were separated and the aqueous layer was extracted with ethyl acetate. The combined organic layers was washed with brine, dried and concentrated to give a tan oil. Flash column chromatography (25 g silica gel column) up to 100% ethyl acetate/hexane afforded the desired product (112 mg, 62%). $^1$H NMR (400 MHz, CHLOROFORM-d) δ ppm 8.53 (dd, J=4.91, 1.64 Hz, 1H) 7.85 (dd, J=7.68, 1.64 Hz, 1H) 7.34 (dd, J=7.68, 4.91 Hz, 1H) 7.00-7.16 (m, 3H) 5.32 (s, 1H) 4.94-5.04 (m, 1H) 4.48 (dd, J=11.83, 3.02 Hz, 1H) 2.14-2.48 (m, 4H); 19F NMR (376 MHz, CHLOROFORM-d) δ ppm −138.24−−138.07 (m, 1F) −140.70−−140.50 (m, 1F).

Intermediate 2

(5S,6S,9R)-6-(2,3-difluorophenyl)-9-(triisopropylsilyloxy)-6,7,8,9-tetrahydro-5H-cyclohepta[b]pyridin-5-ol

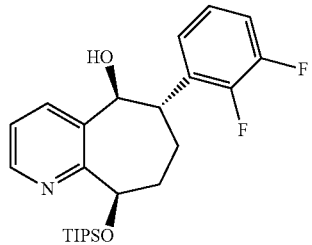

(Int-2)

Lithium borohydride (0.982 g, 45.1 mmol) was added to a cyclopentyl methyl ether (30 mL) solution of (6S,9R)-6-(2,3-difluorophenyl)-9-(triisopropylsilyloxy)-6,7,8,9-tetrahydro-5H-cyclohepta[b]pyridin-5-one (5.0224 g, 11.27 mmol) at 0° C. under N$_2$. The reaction mixture was stirred at 0° C. for 2 hours and then an addition 4 hours at room temperature. The reaction was quenched by adding methanol. The reaction mixture was stirred for 0.5 hour. The solvent was mostly removed via vacuum and the crude material was taken up in ethyl acetate, which was washed with water three times. Flash column by ethyl acetate in hexane from 0 to 10% gave the desired product (3.28 g, 65%).

Intermediate 3

(5R,6S,9R)-5-chloro-6-(2,3-difluorophenyl)-9-(triisopropylsilyloxy)-6,7,8,9-tetrahydro-5H-cyclohepta[b]pyridine

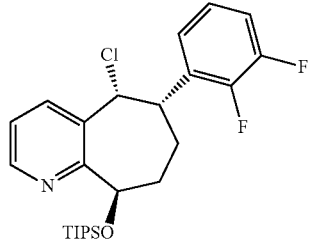

(Int.3)

In an oven-dried 250 mL round-bottom flask was suspended NCS (0.751 g, 5.62 mmol) in tetrahydrofuran (15 mL). Triphenylphosphine (1.475 g, 5.62 mmol) was added. After stirring under nitrogen for 5 min, (5S,6S,9R)-6-(2,3-difluorophenyl)-9-(triisopropylsilyloxy)-6,7,8,9-tetrahydro-5H-cyclohepta[b]pyridin-5-ol (1.007 g, 2.250 mmol) was added in one portion to the gray suspension. The resulting reddish suspension was stirred at room temperature. The solids gradually dissolved to give a tan solution. After 5 h, LCMS indicated complete conversion. Tetrahydrofuran was removed in vacuo and the remaining red oil was directly purified by ISCO (240 g silica column) up to 60% ethyl acetate/hexane. Pure ethyl acetate eluted the non polar component and the product was eluted by 10% methanol (with 2.0M NH$_4$OH) in methylene chloride. The product fractions were combined and re-purified by FCC up to 50% ethyl acetate/hexane to afford the desired product as a colorless oil (869 mg, 83%). MS (ESI) [M+H$^+$]=466.22; $^1$H NMR (400 MHz, CHLOROFORM-d) δ ppm 8.55 (d, J=3.53 Hz, 1H) 7.63 (br. s., 1H) 7.20 (dd, J=7.68, 4.91 Hz, 1H) 7.01-7.15 (m, 1H) 6.90-7.01 (m, 1H) 6.66-6.90 (m, 1H) 5.55-5.85 (m, 1H) 5.40-5.56 (m, 1H) 3.96-4.33 (m, 1H) 2.33 (br. s., 3H) 2.09-2.20 (m, 1H) 1.14-1.23 (m, 3H) 1.04-1.14 (m, 9H) 1.01 (d, J=7.30 Hz, 9H).

Intermediate 4

(5S,6S,9R)-5-azido-6-(2,3-difluorophenyl)-9-(triisopropylsilyloxy)-6,7,8,9-tetrahydro-5H-cyclohepta[b]pyridine

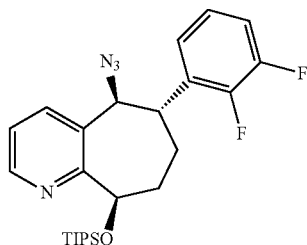

(Int.4)

In a 100 mL round-bottom flask was dissolved (5R,6S,9R)-5-chloro-6-(2,3-difluorophenyl)-9-(triisopropylsilyloxy)-6,7,8,9-tetrahydro-5H-cyclohepta[b]pyridine (566 mg, 1.214 mmol) in dimethylformamide (5 mL) to give a colorless solution. Sodium azide (474 mg, 7.29 mmol) was added, and the mixture was stirred at room temperature under nitrogen for 2.5 h. LCMS indicated only partial reaction. The mixture was heated at 50° C. overnight. After 15 h, LCMS indicated complete conversion with some elimination product. The mixture was diluted with water and ethyl acetate. The layers were separated. The organic layer was washed with brine, dried, and concentrated to give a colorless oil. The crude product was carried onto the next reaction without further purification and characterization. Smaller scale purification afforded an analytical sample: MS (ESI) [M+H$^+$]=473.27; $^1$H NMR (400 MHz, CHLOROFORM-d) δ ppm 8.52-8.63 (m, 1H) 7.75 (d, J=7.81 Hz, 1H) 7.23-7.36 (m, 1H) 6.95-7.17 (m, 2H) 6.89 (br. s., 1H) 5.28 (d, J=4.03 Hz, 1H) 4.90 (d, J=9.07 Hz, 1H) 3.79 (t, J=9.44 Hz, 1H) 1.86-2.23 (m, 4H) 1.16-1.30 (m, 3H) 0.98-1.15 (m, 18H); 19F NMR (376 MHz, CHLOROFORM-d) δ ppm −137.68−−137.36 (m, 1F) −141.78−−141.54 (m, 1F).

Intermediate 5

(5S,6S,9R)-5-azido-6-(2,3-difluorophenyl)-6,7,8,9-tetrahydro-5H-cyclohepta[b]pyridin-9-ol

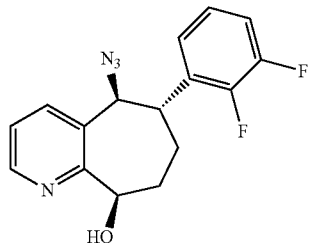

(Int-5)

In a 100 mL round-bottom flask was dissolved (5S,6S,9R)-5-azido-6-(2,3-difluorophenyl)-9-(triisopropylsilyloxy)-6,7,8,9-tetrahydro-5H-cyclohepta[b]pyridine (0.732 g, 1.549 mmol) (crude) in tetrahydrofuran (8 mL) to give a colorless solution. TBAF (1.859 mL, 1.859 mmol) was added, and the resulting light yellow solution was stirred at room temperature for 1.5 h. LCMS indicated complete conversion. Tetrahydrofuran was removed and the residue was diluted with water and ethyl acetate. The layers were separated. The organic layer was washed with brine, dried, and concentrated to give a light yellow oil. Purification by FCC up to 60% ethyl acetate/hexane afforded the desired product (crude weight: 480 mg) as a colorless oil. Smaller scale purification afforded an analytical sample: MS (ESI) [M+H$^+$]=317.22; $^1$H NMR (400 MHz, CHLOROFORM-d) δ ppm 8.51 (dd, J=4.91, 1.38 Hz, 1H) 7.99 (d, J=7.30 Hz, 1H) 7.35 (dd, J=7.81, 5.04 Hz, 1H) 7.06-7.20 (m, 2H) 6.94-7.05 (m, 1H) 5.91 (br. s., 1H) 5.03 (d, J=10.32 Hz, 1H) 4.92 (dd, J=11.21, 2.39 Hz, 1H) 2.84-3.02 (m, 1H) 2.37-2.49 (m, 1H) 2.25-2.36 (m, 1H) 2.07-2.17 (m, J=14.38, 4.94, 3.05, 3.05 Hz, 1H) 1.40-1.64 (m, 1H); $^{13}$C NMR (101 MHz, CHLOROFORM-d) δ ppm 158.48 (s, 1C) 152.19-149.87 (dd, J=13.10 and 221 Hz, 1C) 149.72-147.42 (dd, J=13.87 and 219 Hz, 1C) 146.16 (s, 3C) 133.67 (s, 2C) 133.23 (s, 1C) 132.66 (d, J=10.79 Hz, 1C) 124.43 (dd, J=6.94, 3.85 Hz, 2C) 123.84 (br. s., 1C) 122.89 (s, 2C) 115.98 (d, J=17.73 Hz, 2C) 70.94 (s, 3C) 65.67 (s, 1C) 45.43 (br. s., 1C) 35.71 (s, 3C) 33.45 (s, 2C); 19F NMR (376 MHz, CHLOROFORM-d) δ ppm −137.55-−137.20 (m, 1F) −142.28-−141.89 (m, 1F).

Intermediate 6

(5S,6S,9R)-5-azido-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate

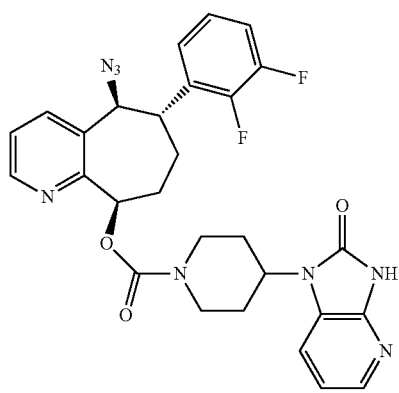

(Int.6)

In a 100 mL round-bottom flask was dissolved (5S,6S,9R)-5-azido-6-(2,3-difluorophenyl)-6,7,8,9-tetrahydro-5H-cyclohepta[b]pyridin-9-ol (0.490 g, 1.549 mmol) (azeotroped with dry benzene) and 4-nitrophenyl 4-(2-oxo-2,3-dihydro-1H-imidazo[4,5-b]pyridin-1-yl)piperidine-1-carboxylate (0.713 g, 1.859 mmol) in dimethylformamide (8 mL) to give a light yellow suspension under nitrogen. After cooling to −15° C. (ice-methanol bath), NaHMDS (4.18 mL, 4.18 mmol) was added dropwise. The resulting tan solution was stirred under nitrogen at −10° C. to 0° C. for 2 h and at room temperature for 2 h. LCMS showed complete conversion. The reaction was quenched with sodium bicarbonate solution. The mixture was diluted with ethyl acetate. The layers were separated and the aqueous layer was extracted with ethyl acetate. The combined organic layers were washed with water, brine, dried with sodium sulfate, and concentrated to give a tan oil. Purification by FCC up to 8% methanol/methylene chloride afforded the desired product (major peak, 632 mg, 73% for 3 steps) as a light yellow foam. MS (ESI) [M+H$^+$]=561.27; $^1$H NMR (400 MHz, CHLOROFORM-d) δ ppm 11.50 (br. s., 1H) 8.58 (d, J=3.78 Hz, 1H) 8.11 (d, J=5.04 Hz, 1H) 7.91 (d, J=7.30 Hz, 1H) 7.33 (br. s., 2H) 7.07-7.19 (m, 2H) 6.92-7.06 (m, 2H) 6.10 (d, J=9.32 Hz, 1H) 5.23 (d, J=10.07 Hz, 1H) 4.26-4.84 (m, 3H) 2.46-3.34 (m, 4H) 2.20-2.43 (m, 3H) 2.01-2.13 (m, 1H) 1.94 (d, J=12.34 Hz, 3H); 19F NMR (376 MHz, CHLOROFORM-d) δ ppm −137.30-−137.01 (m, 1F) −142.32-−142.03 (m, 1F).

Compound (I)

(5S,6S,9R)-5-amino-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate

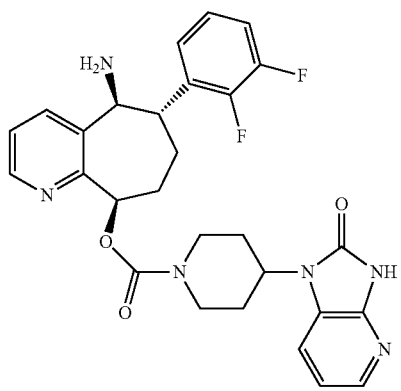

(I)

In a 100 mL round-bottom flask was dissolved (5S,6S,9R)-5-azido-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl)piperidine-1-carboxylate (620 mg, 1.106 mmol) (Intermediate 6) in tetrahydrofuran (5 mL) to give a colorless solution. Trimethylphosphine (3.32 mL, 3.32 mmol, 1.0 M in toluene) was added. The mixture was stirred at room temperature. After 2 h, LCMS showed no starting material. Water (0.080 mL, 4.42 mmol) was added, and the mixture was stirred for another 3 h. LCMS showed complete conversion to the desired product. Volatile components were removed in vacuo and the residue was directly purified by FCC up to 10% methanol in methylene chloride to afford the product (510 mg, 85%) as a white solid. MS (ESI) [M+H$^+$]=535.23; $^1$H NMR (400 MHz, CHLOROFORM-d) δ ppm 10.39 (br. s., 1H) 8.52 (d, J=3.78 Hz, 1H) 8.09 (d, J=5.04 Hz, 2H) 7.46 (br. s., 1H) 7.26-7.38 (m, 1H) 7.06-7.20 (m, 3H) 6.94-7.05 (m, 1H) 6.06-6.23 (m, 1H) 4.31-4.78 (m, 4H) 4.05 (spt, J=6.13 Hz, 1H) 2.57-3.25 (m, 3H) 2.17-2.38 (m, 3H) 1.42-2.04 (m, 6H); 19F NMR (376 MHz, CHLOROFORM-d) δ ppm −136.90 (br. s., 1F) −142.48-−142.21 (m, 1F).

High Throughput Salt Screening for Crystalline Salts of Compound (I)

High throughput crystallization was employed to screen for the formation of crystalline salts of Compound (I). The screening examined acid type, acid level (equivalents), and/or type of crystallization solvent. Each plate contained 96 well plates (8 rows of 12 columns per plate).

A solution was prepared by dissolving 400 mg of Compound (I) in a mixture of 36 ml THF and 4 mL $H_2O$. The solution (12.5 mL) was transferred to 24 vials. To each vial was added 0.25 M EtOH stock solutions of the following acids:

| | | |
|---|---|---|
| 1 eq. acetic acid | 1 eq. L-lactic acid | 2 eq. succinic acid |
| 1 eq. benzoic acid | 1 eq. maleic acid | 0.5 eq. sulfuric acid |
| 1 eq. benzenesulfonic acid | 1 eq. L-malic acid | 1 eq. sulfuric acid |
| 1 eq. citric acid | 1 eq. methanesulfonic acid | 1 eq. sulfuric acid |
| 1 eq. fumaric acid | 2 eq. methanesulfonic acid | 2 eq. sulfuric acid |
| 2 eq. fumaric acid | 1 eq. phosphoric acid | 1 eq. D-tartaric acid |
| 1 eq. hydrochloric acid | 2 eq. phosphoric acid | 1 eq. L-tartaric acid |
| 2 eq. hydrochloric acid | 1 eq. succinic acid | 2 eq. L-tartaric acid |

The content of each vial was transferred to 12 crystallization wells and evaporated to dryness. Upon evaporation, each well was charged with 100 μl of solvent using a robotic liquid handler. The following crystallization solvents were tested: methyl isobutyl ketone (MIBK), ethyl acetate, toluene, THF, acetonitrile, acetone, isopropanol, ethanol, methanol, 1,2-dichloroethylene, isopropanol/water (50:50), and water. Next, the plates were sealed with Teflon septa and subjected to temperature cycling. The plates were maintained at 50° C. for 10 hours and then allowed to cool to room temperature over a period of 14 hours. After the heating/cooling cycle, the contents of the wells were characterized by birefringent imaging. Perceived crystalline hits were further characterized by PXRD analysis.

Crystalline salt formation was not observed for Compound (I) in the presence of acetic acid, benzoic acid benzenesulfonic acid, L-lactic acid, maleic acid, L-malic acid, phosphoric acid, and succinic acid. Crystalline salt formation was observed for Compound (I) in the presence of citric acid, fumaric acid, hydrochloric acid, methanesulfonic acid, sulfuric acid, D-tartaric acid, and L-tartaric acid, in at least one solvent. The properties of the crystalline salts of Compound (I) were characterized further.

The results of the salt screen and crystalline salt characterization are shown in Table 3.

TABLE 3

| Acid | Equiv. | Observations |
|---|---|---|
| Acetic acid | 1 | No crystalline salt formation. |
| Benzoic acid | 1 | No crystalline salt formation. |
| Benzenesulfonic acid | 1 | No crystalline salt formation. |
| Citric acid | 1 | Crystalline salt; hygroscopic at ambient temperature and relative humidity conditions. PXRD patterns of slurry and dried material did not match. |
| Fumaric acid | 1, 2 | Crystalline salt; hygroscopic at ambient temperature and relative humidity conditions; samples contained about 6 wt. % water at >25% relative humidity. |
| Hydrochloric acid | 1, 2 | Crystalline salt; crystals were hygroscopic at ambient temperatures and relative humidity conditions; crystalline salt samples included multiple hydration states and multiple crystalline forms. Solid state NMR indicated that prepared samples contained mixture of crystalline phases. |
| L-lactic acid | 1 | No crystalline salt formation. |
| Maleic acid | 1 | No crystalline salt formation. |
| L-malic acid | 1 | No crystalline salt formation. |
| Methanesulfonic acid | 1, 2 | Crystalline salt obtained in salt screen. Unable to scale-up preparation of crystalline salt for >40 mg samples. Scale-up yielded mixture of amorphous salt and free base. |
| Phosphoric acid | 1, 2 | No crystalline salt formation observed in high throughput screening. Phosphate salt was isolated in manual salt screening study, but converted to free base in an EtOH/water slurry. |
| Succinic acid | 1, 2 | No crystalline salt formation. |
| Sulfuric acid | 0.5, 1, 2 | Crystalline hemisulfate salt obtained at 0.5, 1, and 2 equivalents $H_2SO_4$; crystallized reproducibly with high purity and yield; chemically stable; physically stable; low/non-hygroscopic at ambient temperatures and relative humidity conditions. PXRD patterns of slurry and dried material matched. Solid state NMR indicated single phase. |
| D-tartaric acid | 1 | Crystalline salt; non-naturally occurring stereoisomer; expensive material. |
| L-tartaric acid | 1, 2 | Crystalline salt; different PXRD patterns for slurry and dried phases; heated drying of slurry needed to remove solvent efficiently for larger scale process; however, heating results in partial loss of crystallinity and non-reproducibility of drying process |

Example 1

(5S,6S,9R)-5-Amino-6-(2,3-difluorophenyl)-6,7,8,9-tetrahydro-5H-cyclohepta[b]pyridin-9-yl-4-(2-oxo-2,3-dihydro-1H-imidazo[4,5-b]pyridin-1-yl) piperidine-1-carboxylate, Hemisulfate Salt Preparation from Ethanol/Water Solution Compound (I) (1 g) was dissolved in 17 mL of ethanol and water (3:1) at 70° C. (Solution A). Separately, 52 μL of 96% $H_2SO_4$ (0.5 equiv.) was dissolved in 8 mL of ethanol and water (3:1) at room temperature (Solution B). Next, 30 mg of seeds were added to the Solution A. Solution B was added to the seeded Solution A over a period of 2 hours with a syringe pump. The resulting slurry was stirred at 70° C. for 1 hour and cooled to 20° C. over 90 min. The slurry was allowed to stir at room temperature overnight. The slurry was filtered. The wet cake was washed with 8 mL of EtOH:water solution (3:1), and dried at 30° C. in a vacuum oven overnight to afford 1.01 g (88.4 mole %) of Example 1 as a crystalline solid. GADDS showed that crystalline solid was in Form H-1.5.

Preparation from Tetrahydrofuran/Water Solution

Compound (I) (1 g) was dissolved in 10 mL of THF and water (4:1) at 50° C. (Solution A). Separately, 52 μL of 96% $H_2SO_4$ (0.5 equiv.) was dissolved in 10 mL of THF at room temperature (Solution B). Next, 0.5 mL of Solution B was added to Solution A, followed by the addition of 20 mg of seeds. The solution changed into a thin slurry. The remaining quantity of Solution B was to the slurry over a period of 2 hours with a syringe pump. The slurry was stirred at 50° C. for 1 hour and then allowed to cool to 20° C. over a period of 1 hour. The slurry was stirred at room temperature overnight. The slurry was filtered. The wet cake was washed 8 mL of THF:water=3:1, and dried at 30° C. in a vacuum oven overnight to afford 1.06 g (92.8 mole %) of Example 1 as a crystalline solid. GADDS showed that crystalline solid was in Form H-1.5.

Stability Study

The solid state stability of Example 1 was tested by exposing samples to various temperature and relative humidity conditions for periods of 1, 2, and 4 weeks. The % potency (% pot.) and the % total impurities (% total imp.) are shown in Table 4. The results indicate that the crystalline Form H1.5-1 of the hemisulfate salt of Compound (I) is stable under the tested storage conditions as indicated by no significant increase in total impurity levels and/or no decrease in potency after four weeks of storage.

TABLE 4

Solid State Stability of Hemisulfate Salt, Form H1.5-1

|  | Initial | | 1 week | | 2 weeks | | 4 weeks | |
| --- | --- | --- | --- | --- | --- | --- | --- | --- |
|  | % pot. | % total imp. | % pot. | % total imp. | % pot. | % total imp. | % pot. | % total imp. |
| Refrigerated | 98.5 | 0.27 | 98.0 | 0.29 | 96.5 | 0.27 | 105.7 | 0.27 |
| 25 RH/60° C. |  |  | 94.4 | 0.27 | 96.8 | 0.27 | 96.9 | 0.27 |
| 25 RH/60° C. |  |  | 95.1 | 0.27 | 98.5 | 0.27 | 97.0 | 0.27 |
| 25 RH/60° C. |  |  | 101.6 | 0.28 | 102.6 | 0.27 | 110.0 | 0.27 |
| HIL/UV |  |  | 100.7 | 0.27 | 96.9 | 0.27 | — | — |

Figure 5:
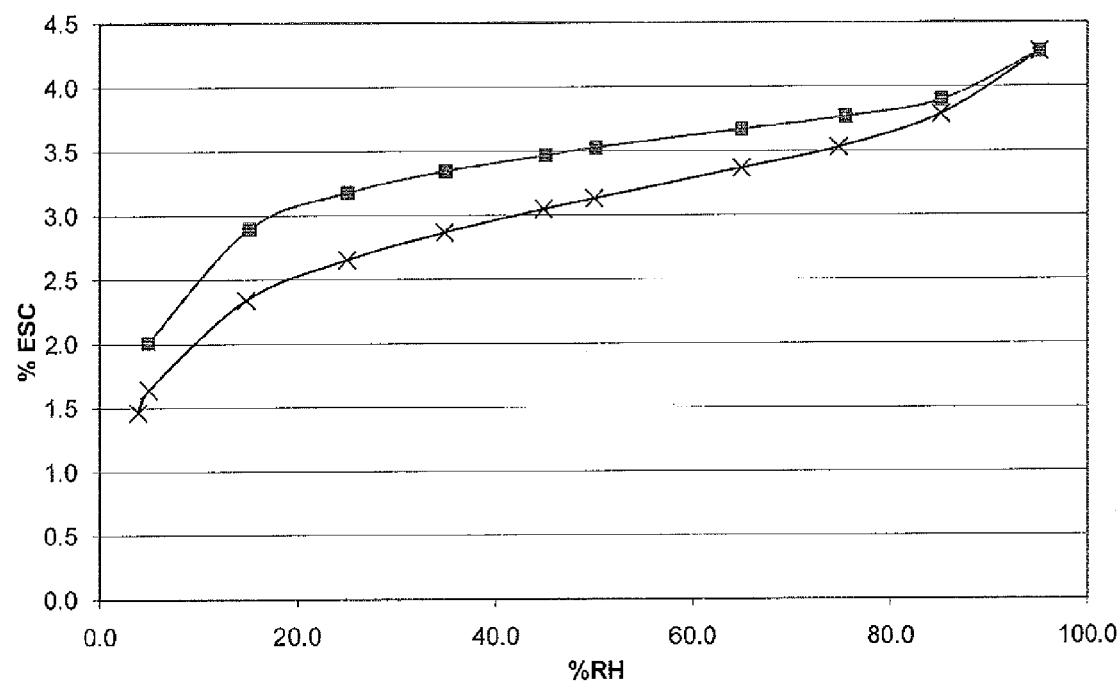
FIG. 5 shows the moisture sorption isotherm for Example 1 at 25° C. (X) adsorption; (■) desorption.
Figure 6:
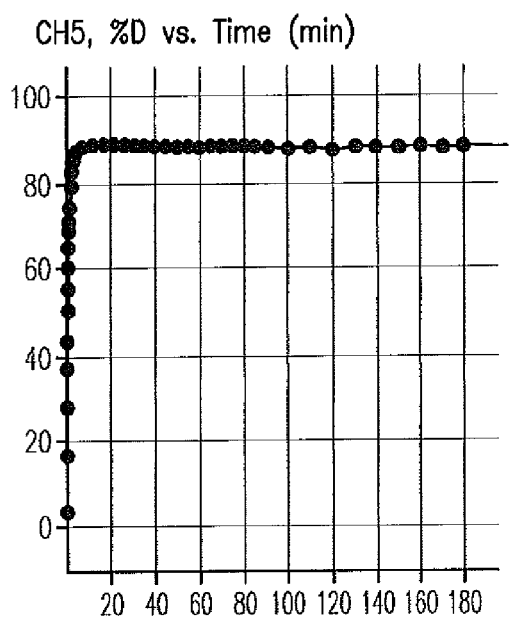
FIG. 6 shows the % dissolution versus time at a pH value of approximately 5 in fed state simulated intestinal fluid (FeSSIF) and a pH value of approximately 7 in fasted state simulated intestinal fluid (FaSSIF) for Compound (I) as free base and the HCl salt of Compound (I).
Figure 6:
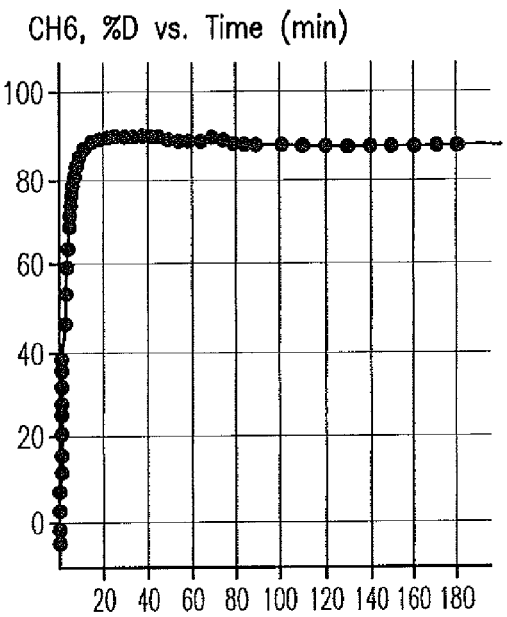
Figure 6:
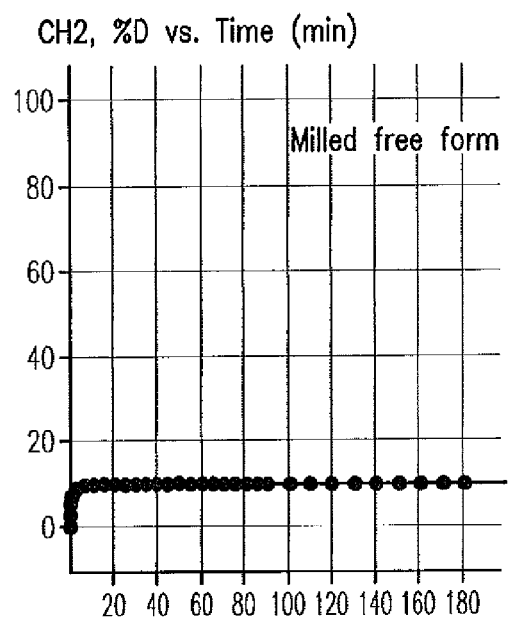
Figure 6:
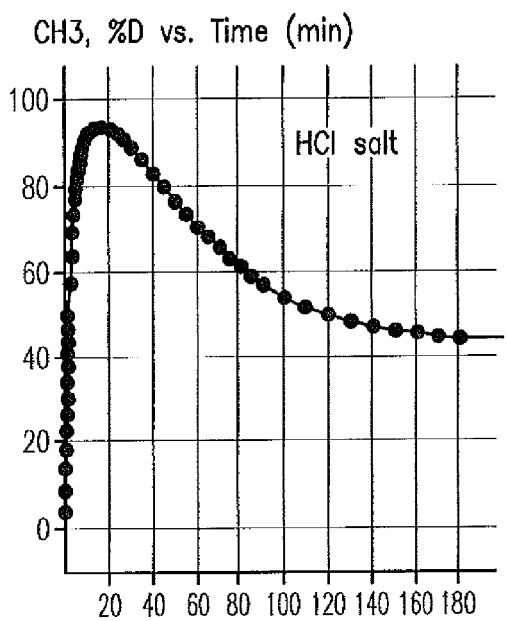
Figure 7:
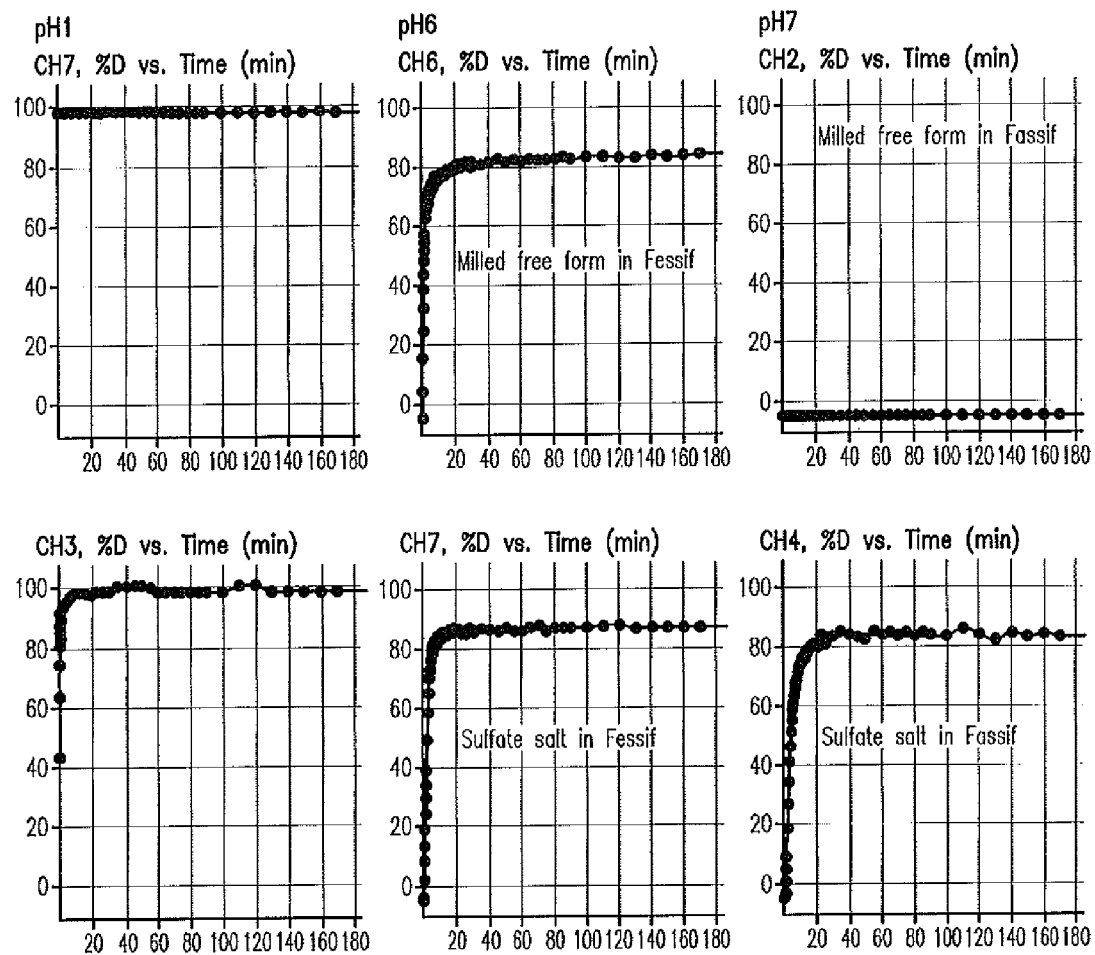
FIG. 7 shows the % dissolution versus time at a pH value of approximately 1, a pH value of approximately 5 in fed state simulated intestinal fluid (FeSSIF), and a pH value of approximately 7 in fasted state simulated intestinal fluid (FaSSIF) for Compound (I) as free base and the hemisulfate salt of Compound (I).

% pot. = % potency
% total imp. = % total impurities
HIL/UV: high-intensity light/ultraviolet The moisture sorption isotherm for Example 1 is shown in FIG. 5. Example 1 has moisture sorption weight gains of 0.8 weight % and 2.8 weight % between 25% and 75% relative humidity and 5% and 95% relative humidity, respectively. These results indicated that the hemisulfate salt of Compound (I) is low or non-hygroscopic under the tested conditions Form H1.5-1

Table 5 shows characteristic PXRD diffraction peak positions (degrees 2θ±0.1) measured at about 25° C. for Example 1, based on a high quality pattern collected with a diffractometer (CuKα) with a spinning capillary with 2θ calibrated with a NIST other suitable standard.

TABLE 5

PXRD Peak Positions (degrees 2θ ± 0.1)

| | |
| --- | --- |
| 5.4 | 17.6 |
| 8.6 | 18.1 |
| 9.7 | 20.5 |
| 12.4 | 21.4 |
| 14.9 | 22.0 |

Table 6 shows characteristic solid state NMR peak positions δ (ppm) for Example 1, referenced to TMS.

TABLE 6 ssNMR peak positions - δ (ppm)

| | | |
| --- | --- | --- |
| 26.6 | 72.5 | 140.8 |
| 27.1 | 117.0 | 144.7 |
| 28.3 | 117.7 | 148.7 |
| 30.7 | 124.2 | 149.8 |
| 43.1 | 125.2 | 151.2 |
| 45.9 | 128.3 | 153.4 |
| 47.1 | 130.3 | 155.1 |
| 52.0 | 131.4 | 155.6 |
| 54.2 | 134.1 | 156.7 |

Other Crystalline Forms of Example 1

Form P22C: prepared by heating Form H1.5-1 at 60° C. for 2 hours or at 75° C. for 5 minutes. Water activity studies between Form H1.5-1 and Form P22C showed that Form H1.5-1 is more stable at >23% relative humidity.

Form P33: Form H1.5-1 converted to Form P33 between 50° C. and 75° C. in variable temperature PXRD experiment. Also observed after Form H1.5-1 was heated to 105° C. for 5 minutes, or prepared by slurring dry powder Form H1.5-1 in dry EtOH or IPAc. Elemental analysis indicated that Form P33 is a hemisulfate monohydrate. Solid state NMR indicated that Form P33 was a single phase. Water activity studies between Form H1.5-1 and Form P33 showed that Form H1.5-1 is more stable at >23% relative humidity.

Form P35: Prepared from slurry of Form H1.5-1 in dry MeOH under molecular sieves (7% RH). Converted to Form P33 when dried at 60° C.

Stability in Water Slurry

An aqueous slurry of Example 1 was prepared and stored at room temperature. After two days, there was no significant chemical degradation; and no change in the PXRD pattern, which indicated that the crystalline Form H1.5-1 was stable in the aqueous slurry.

No significant changes were observed in the thermogravimetric scan and the differential scanning calorimetry scan, and in the PXRD.

The hemisulfate salt of Compound (I) has been compared to other salts of Compound (I) and has been found to be especially advantageous. The hemisulfate salt of Compound (I) has the surprising advantage of providing a salt that is physically stable and chemically stable compared to other salts of Compound (I). Further, the hemisulfate salt had the surprising advantage of being provided in a stable crystalline form, Form H1.5-1. For example, the hemisulfate salt of Compound (I) was reproducibly prepared as a crystalline form, had low hygroscopicity, and did not readily change crystalline form or hydration state in response to changes in relative humidity and/or temperature. In contrast, the citric acid salt, fumaric acid salt, hydrochloric acid salt, methanesulfonic acid salt, phosphoric acid salt, and L-tartaric acid salt were hygroscopic at ambient temperature and relative humidity conditions, resulting is weight changes, hydration state changes, and/or phase changes. Crystalline salt formation was not observed for Compound (I) in the presence of acetic acid, benzoic acid, benzenesulfonic acid, L-lactic acid, maleic acid, L-malic acid, and succinic acid in the high throughput salt screening. Further, the preparation of the hemisulfate salt did not require use of an expensive material such as D-tartaric acid.

Biological Methods

In Vitro Pharmacology.

Tissue Culture.

SK-N-MC cells were grown at 37° C. in 5% $CO_2$ as a monolayer in medium consisting of MEM with Earle's salts and L-glutamine (Invitrogen) supplemented with 10% fetal bovine serum (Invitrogen).

Membrane Preparation.

Crude membranes were prepared from SK-N-MC cells expressing CGRP receptors. The cells were rinsed twice with phosphate-buffered saline (155 mM NaCl, 3.3 mM $Na_2HPO_4$, 1.1 mM KHYDROGENPO$_4$, pH 7.4), and incubated for 5-10 min. at 4° C. in hypotonic lysis buffer consisting of 10 mM Tris (pH 7.4) and 5 mM EDTA. The cells were transferred from plates to polypropylene tubes (16×100 mm) and homogenized using a polytron. Homogenates were centrifuged at 32,000×g for 30 min. The pellets were resuspended in cold hypotonic lysis buffer with 0.1% mammalian protease inhibitor cocktail (Sigma) and assayed for protein concentration. The SK-N-MC homogenate was aliquoted and stored at –80° C.

Radioligand Binding Assay.

Compound (I) was solubilized and carried through serial dilutions using 100% DMSO. Aliquots from the compound serial dilutions were further diluted 25 fold into assay buffer (50 mM Tris-Cl pH 7.5, 5 mM $MgCl_2$, 0.005% Triton X-100) and transferred (volume 50 μl) into 96 well assay plates. [$^{125}$I]-CGRP (GE Healthcare or Perkin-Elmer) was diluted to 72 pM in assay buffer and a volume of 50 μl was added to each well. SK-N-MC membranes were thawed, diluted in assay buffer with fresh 0.1% mammalian protease inhibitor cocktail (Sigma), and re-homogenized. SK-N-MC homogenate (7 μg/well) was added in a volume of 100 μl. The assay plates were then incubated at room temperature for 2 h. Assays were stopped by addition of excess cold wash buffer (50 mM Tris-Cl pH 7.5, 0.1% BSA) immediately followed by filtration over glass fiber filters (Whatman GF/B) previously soaked in 0.5% PEI. Non-specific binding was defined with 1 μM beta-CGRP (Bachem). Protein bound radioactivity was determined using a gamma or scintillation counter. The resulting data was analyzed using a four parameter competitive binding equation (XLfit v2.0) and the $IC_{50}$ was defined as the concentration of Compound (I) required to displace 50% of radioligand binding. Final assay concentration of [$^{125}$I]-CGRP was 18 pM. The mean $K_d$ for [$^{125}$I]-CGRP is 25.4 pM. Compound (I) was evaluated in at least two separate experiments. In this study, the Human CGRP Receptor $IC_{50}$ value of Compound (I) was 0.04 nM.

In Vivo Pharmacokinetic Studies

An in vivo study was conducted comparing the pharmacokinetics of the free base Compound (I) in humans pretreated with 40 mg of famotidine with non-pretreated humans.

Compound (I) in human EDTA plasma was analyzed using liquid-liquid extraction with uHPLC-MS/MS detection on a Triple Quad 5500 mass spectrometer. The method utilized stable isotope labeled [$^{13}C_2$, $D_4$]-Compound (I) as the internal standard. After the addition of 50 μL of 100 ng/mL [$^{13}C_2$, $D_4$]-Compound (I) in MeOH:water (20/80) and of 50 μL 1M NH4OAc containing 4% acetic acid buffer solution to 0.100 mL of each study sample, quality control (QC) sample, and calibration standard, the samples were extracted with 600 μL methyl tert-butyl ether (MTBE) by shaking for 15 min. A 450 μL portion of the organic layer was removed and evaporated to dryness. The residue was reconstituted in 200 μL of the reconstitution solution (30% acetonitrile in 10 mM NH4OAc with 0.01% acetic acid). All liquid transfer steps were performed using a Perkin Elmer JANUS Mini® liquid handler except for the addition of the internal standard solution. A 10 μL aliquot of the extracted sample was injected to uHPLC-MS/MS system. The uHPLC was performed on a LEAP 4X Ultra uHPLC system with LEAP HTC PAL autosampler. Mobile phase A contained 10 mM NH$_4$OAc and 0.01% acetic acid in ACN/water (10:90), and mobile phase B contained 10 mM NH$_4$OAc and 0.01% acetic acid in ACN/water (90:10). Chromatographic separation was achieved on an Acquity® uHPLC BEH C18 column (1.7 μm, 2.1×50 mm) with an isocratic elution from 0-1.5 min consisted of 28% Mobile Phase B for analysis of Compound (I), then with a gradient elution consisted of a linear increase from 28% B to 100% B in 0.1 min, then maintaining it at 100% B for 1.1 min for washing out the column. The gradient was then returned to 28% B within 0.1 min, and maintained at 28% for 0.9 min with a total run time of 3.7 min. The flow rate was 0.6 mL/min and column temperature was maintained at 60° C. condition. Detection was accomplished using an AB Sciex Triple Quad 5500 mass spectrometer in positive ESI with turbo ion spray ionization and using multiple reaction monitoring (MRM) mode. The MRM transitions were m/z 535→256 for Compound (I) and m/z 541→256 for [$^{13}C_2$, $D_4$]-Compound (I). Data acquisition and quantiation were performed using AB Sciex Analyst® 1.5.1 software. The standard curve, which ranged from 0.500-500 ng/ml for Compound (I), was fitted to a 1/x2 weighted linear regression model. During sample analysis, four levels of analytical quality control (QC) samples representing low, geometric-mean, medium, and high concentrations of Compound (I) prepared in human EDTA plasma were analyzed in 4 replicates at each concentration level for each analytical run. The results from these QC samples were used to accept or reject the analytical runs containing study samples based on the acceptance criteria established a priori for the analysis of Compound (I) in human EDTA plasma.

Figure 8:
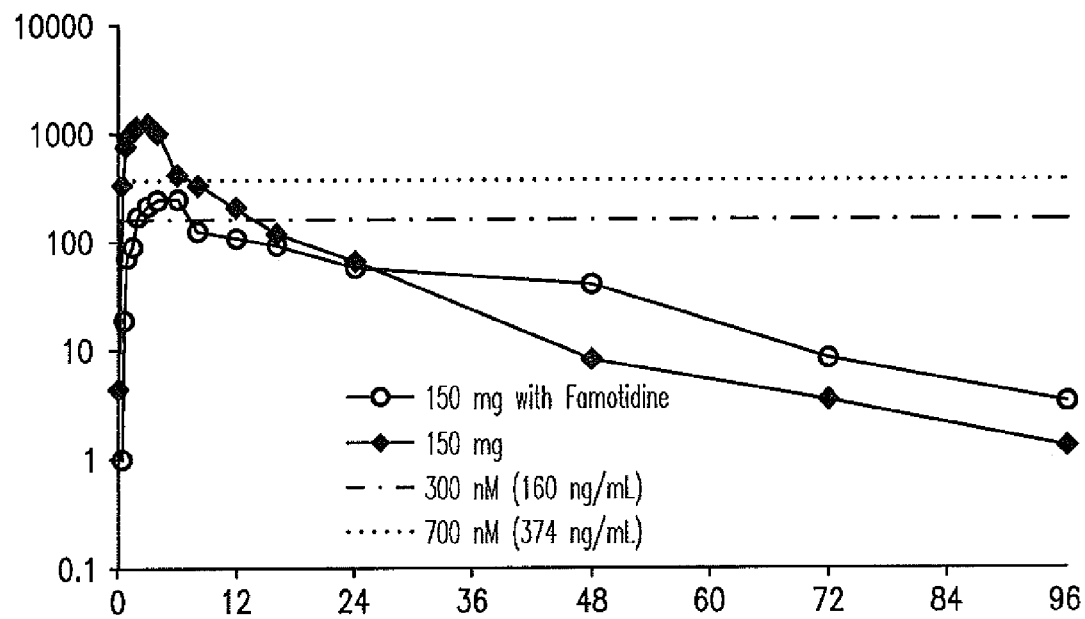
FIG. 8 shows plasma pharmacokinetics of Compound (I), free base, in humans after oral administration, with and without pretreatment with famotidine (40 mg) two hours prior to administration of Compound (I). Compound (I) was administered at a dose of 150 mg. (●) Compound (I) (nM); (♦) Compound (I) with famotidine pretreatment (nM). The x-axis is time in minutes.

The results of this study are show in Table 7 and FIG. 8. A significant reduction in AUC and Cmax of Compound (I) was observed in humans pretreated with 40 mg of famotidine compared to non-pretreated humans.

TABLE 7

| Dose | 150 mg Compound (I) | 150 mg Compound (I) with 40 mg Famotidine |
|---|---|---|
| $C_{max}$ (ng/mL) | 991 (85%) | 259 (35%) |
| $T_{max}$ Median (min-max) | 2.5 (0.75-3.0) | 3 (2.0-4.0) |
| AUC inf (ng * hr/mL) | 7197 (75%) | 3058 (27%) |
| Half Life (hr) | 12.04 (29%) | 12.6 (36%) |
| Cl/F (L/hr) | 20.84 (75%) | 49 (28%) |
| F ($AUC_{inf}$) | — | 42.5% (96%) |
| F ($C_{max}$) | — | 26.2% (130%) |

An in vivo study was conducted comparing the pharmacokinetics of the free base Compound (I) and the hemisulfate salt of Compound (I) in dogs pretreated with famotidine or pentagastrin.

Capsules were prepared containing either 150 mg of Compound (I) as the free base or as the hemisulfate salt of Compound (I):

1. Compound (I) free base capsules: 50 wt. % Compound (I), 42 wt. % microcrystalline cellulose, 3 wt. % croscarmellose sodium, 4 wt. % Klucel EXF hydroxypropylcellulose, 0.5 wt. % magnesium stearate, 0.5 wt. % colloidal silicon dioxide 2. Compound (I) hemisulfate salt capsules: 57% Example 1 (hemisulfate salt of Compound (I), in crystalline form H1.5-1), 40% microcrystalline cellulose, 3% Croscarmellose sodium.

Four male dogs (10 kg) were treated according to the following three treatment protocols:

Treatment 1: pretreatment with pentagastrin (6 μg/kg, IP) several hours prior to the oral administration of Compound (I) free base capsule.

Treatment 2: pretreatment with 40 mg famotidine orally, three hours prior to the oral administration of Compound (I) free base capsule.

Treatment 3: pretreatment with 40 mg famotidine orally, three hours prior to the oral administration of Compound (I) hemisulfate salt capsule.

Blood samples were collected at 0, 0.5, 1, 2, 4, 8, and 24 hours after administration of the Compound (I) free base capsule or Compound (I) hemisulfate salt capsules and stored in EDTA tubes. Compound (I) in dog EDTA plasma was analyzed using liquid-liquid extraction and uHPLC-MS/MS detection on a Triple Quad 5500 mass spectrometer. An aliquot of 0.050 mL of dog EDTA plasma was used for the assay. The method utilized stable isotope labeled [$^{13}C_2$, $D_4$]-Compound (I) as the internal standard. After the addition of 50 μL of 200 ng/mL [$^{13}C_2$, $D_4$]-Compound (I) in MeOH:water (20/80) and of 50 μL 1M NH4OAc containing 4% acetic acid buffer solution to 0.050 mL of each study sample, quality control (QC) sample, and calibration standard, the samples were extracted with 600 μL methyl tert-butyl ether (MTBE) by shaking for 15 min. A 450 μL portion of the organic layer was removed and evaporated to dryness. The residue was reconstituted in 300 μL of the reconstitution solution (30% acetonitrile in 10 mM NH4OAc with 0.01% acetic acid). All liquid transfer steps were performed using a Perkin Elmer JANUS Mini® liquid handler except for the addition of the internal standard solution. A 5 μL aliquot of the extracted sample was injected to uHPLC-MS/MS system. The uHPLC was performed on a LEAP 4X Ultra uHPLC system with LEAP HTC PAL autosampler. Mobile phase A contained 10 mM $NH_4OAc$ and 0.01% acetic acid in ACN/water (10:90), and mobile phase B contained 10 mM $NH_4OAc$ and 0.01% acetic acid in ACN/water (90:10). Chromatographic separation was achieved on an Acquity® uHPLC BEH C18 column (1.7 μm, 2.1×50 mm) with an isocratic elution from 0-1.5 min consisted of 28% Mobile Phase B for analysis of Compound (I), then with a gradient elution consisted of a linear increase from 28% B to 100% B in 0.1 min, then maintaining it at 100% B for 1.1 min for washing out the column. The gradient was then returned to 28% B within 0.1 min, and maintained at 28% B for 0.9 min with a total run time of 3.7 min. The flow rate was 0.6 mL/min and column temperature was maintained at 60° C. condition. Detection was accomplished using an AB Sciex Triple Quad 5500 mass spectrometer in positive ESI with turbo ion spray ionization and using multiple reaction monitoring (MRM) mode. The MRM transitions were m/z 535→256 for Compound (I) and m/z 541→256 for [$^{13}C_2$, $D_4$]-Compound (I). Data acquisition and quantification were performed using AB Sciex Analyst® 1.5.1 software. The standard curve, which ranged from 3.00 to 3000 ng/mL for Compound (I), was fitted to a 1/x2 weighted linear regression model. During sample analysis, four levels of analytical quality control (QC) samples representing low, geometric-mean, medium, and high concentrations of Compound (I) prepared in dog EDTA plasma were analyzed in 4 replicates at each concentration level for each analytical run. The results from these QC samples were used to accept or reject the analytical runs containing study samples based on the acceptance criteria established a priori for the analysis of Compound (I) in dog EDTA plasma.

Figure 9:
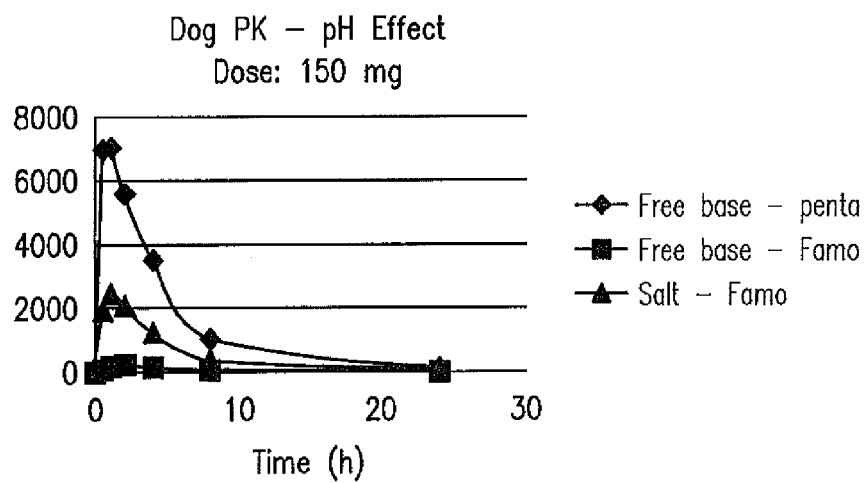
FIG. 9 shows plasma pharmacokinetics of Compound (I) in dogs after the oral administration of Compound (I) and Example 1. Compound (I) and Example 1 were orally administered at a dose of 150 mg (or equivalent). (♦) Compound (I) (nM) and pretreatment with pentagastrin (6 μm/km); (■) Compound (I) and famotidine (40 mg); (▲) Example 1 (hemisulfate salt) and famotidine (40 mg).

The results of this study are show in Table 8 and FIG. 9. A significant reduction in AUC and Cmax was observed in famotidine pre-treated dogs (high stomach pH) after treatment with the free base Compound (I) compared to pentagastrin pre-treated dogs (low stomach pH). Dosing of Example 1, the hemisulfate sesquihydrate salt of Compound (I), in famotidine pre-treated dogs showed a much lower reduction in AUC and Cmax. In this particular study, the hemisulfate salt of Compound (I) provided a $C_{max}$ value of 2596 ng/mL, an $AUC_{0-24hr}$ of 12473 ng·h/mL, and 34.73% bioavailability when administered after pretreatment with famotidine. In contrast, in a similar test, Compound (I) free base provided a $C_{max}$ value of 245 ng/mL, an $AUC_{0-24hr}$ of 1762 ng·h/mL, and 4.54% bioavailability when administered after pretreatment with famotidine.

TABLE 8

Pharmacokinetic Parameters for Dosing in Dogs of 150 mg of Compound (I) as Hemisulfate salt or Free base.

| | $C_{max}$ (ng/mL) | | | $AUC_{0-24\,hr}$ (ng·h/mL) | | BA (%) | | |
|---|---|---|---|---|---|---|---|---|
| | Mean | Std Dev | $T_{max}$ (h) | Mean | Std Dev | Mean | Std Dev | CV (%) |
| Compound (I) + pentagastrin | 8156 | 4423 | 0.75 | 38796 | 15407 | 100 | — | 39.71 |
| Compound (I) + famotidine | 245 | 95 | 2 | 1762 | 392 | 4.54 | 1.01 | 22.23 |
| Example 1 + famotidine | 2596 | 409 | 1 | 13473 | 2098 | 34.73 | 5.41 | 15.57 |

The hemisulfate salt of Compound (I) has been compared to Compound (I) free base and has been found to be especially advantageous. The hemisulfate salt of Compound (I) has the surprising advantage of reducing the variability in the bioavailability of Compound (I) and/or increasing the bioavailability of Compound (I) to the patient. Based on these in vitro and in vivo data, it is expected that the hemisulfate will provide a significant advantage of consistency in bioavailability among patients over the free form. To illustrate, the hemisulfate form provides surprisingly enhanced bioavailability in a patient population that is dosed with medicines that can raise the pH of stomach acids, such as antacids, proton pump inhibitors, or $H_2$-receptor antagonists.

Single Crystal Data (LVL)

Data were collected on a Bruker-Nonius CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package (Otwinowski, Z & Minor, W. (1997) in *Macromolecular Crystallography*, eds. Carter, W. C. Jr. & Sweet, R. M. (Academic, NY), Vol. 276, pp 307-326) in the Collect program suite. (Collect Data collection and processing user interface: Collect: Data collection software, R. Hooft, Nonius B. V., 1998). Alternately, single crystal data were collected on a Bruker-AXS APEX2 CCD system using Cu Kα radiation (λ=1.5418 Å). Indexing and processing of the measured intensity data were carried out with the APEX2 software package/program suite (APEX2 Data collection and processing user interface: APEX2 User Manual, v1.27; BRUKER AXS, Inc., Madison, Wis.).

When indicated, crystals were cooled in the cold stream of an Oxford cryo system (Oxford Cryosystems Cryostream cooler: J. Cosier and A. M. Glazer, J. Appl. Cryst., 1986, 19, 105) during data collection.

The structures were solved by direct methods and refined on the basis of observed reflections using either the SDP software package (SDP, Structure Determination Package, Enraf-Nonius, Bohemia N.Y.) with minor local modifications or the crystallographic packages MAXUS (maXus solution and refinement software suite: S. Mackay, C. J. Gilmore, C. Edwards, M. Tremayne, N. Stewart, K. Shankland. maXus: a computer program for the solution and refinement of crystal structures from diffraction data) or SHELXTL (Sheldrick, GM. 1997, SHELXTL. Structure Determination Programs. Version 5.10 or greater, Bruker AXS, Madison, Wis.).

The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

Single Crystal Data (WFD)

A Bruker SMART 2K CCD diffractometer equipped with graphite-monochromated Cu Kα radiation, (λ=1.54056 Å) was used to collect diffraction data at the room temperature. A full data set was collected using the ω scan mode over the 2θ range with a crystal-to-detector distance of 4.98 cm. An empirical absorption correction utilized the SADABS routine associated with the diffractometer (Bruker AXS. 1998, SMART and SAINTPLUS. Area Detector Control and Integration Software, Bruker AXS, Madison, Wis., USA). The final unit cell parameters were determined using the entire data set.

All structures were solved by direct methods and refined by the full-matrix least-squares techniques, using the SHELXTL software package (Sheldrick, G M. 1997, SHELXTL. Structure Determination Programs. Version 5.10, Bruker AXS, Madison, Wis., USA.). The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$, where w is an appropriate weighting function based on errors in the observed intensities. Difference Fourier maps were examined at all stages of refinement. All non-hydrogen atoms were refined with anisotropic thermal displacement parameters. The hydrogen atoms associated with hydrogen bonding were located in the final difference Fourier maps while the positions of the other hydrogen atoms were calculated from an idealized geometry with standard bond lengths and angles. They were assigned isotropic temperature factors and included in structure factor calculations with fixed parameters.

PXRD (Philips)

About 200 mg were packed into a Philips powder X-ray diffraction (PXRD) sample holder. The sample was tranferred to a Philips MPD unit (45 KV, 40 mA, Cu Kα). Data were collected at room temperature in the 2 to 32 2-theta range (continuous scanning mode, scanning rate 0.03 degrees/sec., auto divergence and anti scatter slits, receiving slit: 0.2 mm, sample spinner: ON)

PXRD (GADDS-NB)

X-ray powder diffraction (PXRD) data were obtained using a Bruker C2 GADDS. The radiation was Cu Kα (40 KV, 40 mA). The sample-detector distance was 15 cm. Powder samples were placed in sealed glass capillaries of 1 mm or less in diameter; the capillary was rotated during data collection. Data were collected for $3 \le 2\theta \le 35°$ with a sample exposure time of at least 1000 seconds. The resulting two-dimensional diffraction arcs were integrated to create a traditional 1-dimensional PXRD pattern with a step size of 0.02 degrees 2θ in the range of 3 to 35 degrees 2θ.

DSC (Open Pan)

Differential scanning calorimetry (DSC) experiments were performed in a TA Instruments™ model Q2000, Q1000 or 2920. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

TGA (Open Pan)

Thermal gravimetric analysis (TGA) experiments were performed in a TA Instruments™ model Q500 or 2950. The sample (about 10-30 mg) was placed in a platinum pan previously tared. The weight of the sample was measured accurately and recorded to a thousand of a milligram by the instrument. The furnace was purged with nitrogen gas at 100 mL/min. Data were collected between room temperature and 300° C. at 10° C./min heating rate.

Solid-State Nuclear Magnetic Resonance (SSNMR)

All solid-state C-13 NMR measurements were made with a Bruker AV-400, 400 MHz NMR spectrometer. High resolution spectra were obtained using high-power proton decoupling and the TPPM pulse sequence and ramp amplitude cross-polarization (RAMP-CP) with magic-angle spinning (MAS) at approximately 12 kHz (A. E. Bennett et al, *J. Chem. Phys.*, 1995, 103, 6951), (G. Metz, X. Wu and S. O, Smith, *J. Magn. Reson. A*, 1994, 110, 219-227). Approximately 70 mg of sample, packed into a canister-design zirconia rotor was used for each experiment. Chemical shifts (δ) were referenced to external adamantane with the high frequency resonance being set to 38.56 ppm (W. L. Earl and D. L. VanderHart, *J. Magn. Reson.*, 1982, 48, 35-54).

VTI (Dry On)

Moisture sorption isotherms were collected in a VTI SGA-100 Symmetric Vapor Analyzer using approximately 10 mg of sample. The sample was dried at 60° C. until the loss rate of 0.0005 wt %/min was obtained for 10 minutes. The sample was tested at 25° C. and 3 or 4, 5, 15, 25, 35, 45, 50, 65, 75, 85, and 95% RH. Equilibration at each RH was reached when the rate of 0.0003 wt %/min for 35 minutes was achieved or a maximum of 600 minutes.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A hemisulfate salt of Compound (I):

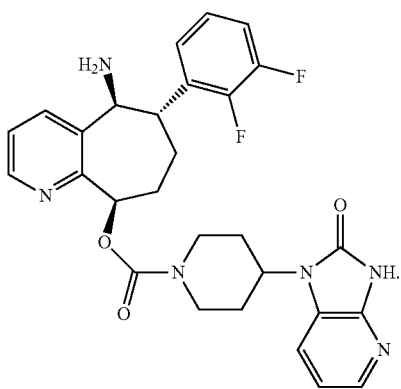

(I)

2. The hemisulfate salt of Compound (I) according to claim 1, wherein said salt of Compound (I) is crystalline.

3. The hemisulfate salt of Compound (I) according to claim 1, wherein said salt Compound (I) is a sesquihydrate.

4. The hemisulfate salt of Compound (I) according to claim 3, wherein said salt comprises crystalline Form H1.5-1.

5. The hemisulfate salt of Compound (I) according to claim 4, wherein said Form H1.5-1 is characterized by one or more of the following:

a) unit cell parameters substantially equal to the following:
Cell dimensions: a=10.92 Å
b=33.04 Å
c=7.90 Å
α=90 degrees
β=90 degrees
γ=90 degrees
Space group: $P2_12_12$
Molecules of Compound (I)/asymmetric unit: I
Volume=2851 Å$^3$
Density (calculated)=1.423 g/cm$^3$,
wherein measurement of said crystalline form is at a temperature of about 25° C.;

b) an observed powder x-ray diffraction pattern substantially in accordance with the pattern shown in FIG. 1;

c) a simulated powder x-ray diffraction pattern substantially in accordance with the pattern shown in FIG. 1;

d) a powder x-ray diffraction pattern (CuKα λ=1.5418 Å) comprising four or more 2θ values selected from: 5.4±0.1, 8.6±0.1, 9.7±0.1, 12.4±0.1, 14.9±0.1, 17.6±0.1, 18.1±0.1, 20.5±0.1, 21.4±0.1, and 22.0±0.1, wherein measurement of the crystalline form is at a temperature of about 25° C.;

and/or e) a solid state nuclear resonance spectra comprising six or more peaks (Γ] (ppm) referenced to TMS) selected from: 26.6±0.1, 27.1±0.1, 28.3±0.1, 30.7±0.1, 43.1±0.1, 45.9±0.1, 47.1±0.1, 52.0±0.1, 54.2±0.1, 72.5±0.1, 117.0±0.1, 117.7±0.1, 124.2±0.1, 125.2±0.1, 128.3±0.1, 130.3±0.1, 131.4±0.1, 134.1±0.1, 140.8±0.1, 144.7±0.1, 148.7±0.1, 149.8±0.1, 151.2±0.1, 153.4±0.1, 155.1±0.1, 155.6±0.1, and 156.7±0.1.

6. A pharmaceutical composition comprising said hemisulfate salt of Compound (I) according to claim 1; and a pharmaceutically acceptable carrier of diluent.

7. The pharmaceutical composition according to claim 6, wherein said hemisulfate salt of Compound (I) is a sesquihydrate.

8. The pharmaceutical composition according to claim 7, wherein said hemisulfate salt of Compound (I) comprises crystalline Form H1.5-1.

* * * * *

UNITED STATES PATENT AND TRADEMARK OFFICE
CERTIFICATE OF CORRECTION

PATENT NO. : 8,759,372 B2
APPLICATION NO. : 13/775528
DATED : June 24, 2014
INVENTOR(S) : Daniel Richard Roberts et al.

It is certified that error appears in the above-identified patent and that said Letters Patent is hereby corrected as shown below:

On the Title Page and In the Specification:

Item (54), and Column 1, lines 1 to 5, change

"*N*-(5S,6S,9R)-AMINO-6-(2,3-DIFLUOROPHENYL)-6,7,8,9-TETRAHYDRO-5H-CTCLOHEPTA[B]PYRIDIN-9-YL-4-(2-OXO-2,3-DIHYDRO-1H-IMIDAZO[4,5-B]PYRIDIN-1-CARBOXYLATE SALT"

to

-- *N*-(5S,6S,9R)-5-AMINO-6-(2,3-DIFLUOROPHENYL)-6,7,8,9-TETRAHYDRO-5H-CYCLOHEPTA[B]PYRIDIN-9-YL-4-(2-OXO-2,3-DIHYDRO-1H-IMIDAZO[4,5-B]PYRIDIN-1-YL)PIPERIDINE-1-CARBOXYLATE SALT --.

In the Claims:

Claim 3:

Column 29, line 33, change "salt Compound (I)" to -- salt of Compound (I) --.

Claim 5:

Column 30, line 23, change "(f] (ppm)" to -- (δ (ppm) --.

Claim 6:

Column 30, line 34, change "of" to -- or --.

Signed and Sealed this
Seventh Day of April, 2015

Michelle K. Lee
*Director of the United States Patent and Trademark Office*